United States Patent
Owen et al.

(10) Patent No.: US 12,358,889 B2
(45) Date of Patent: *Jul. 15, 2025

(54) VAPORIZABLE ALKALOID COMPOSITIONS AND METHODS OF USE THEREOF

(71) Applicant: Ready Mix Naturals, LLC, Seguin, TX (US)

(72) Inventors: Charlotte L. Owen, Seguin, TX (US); Richard Avila, Jr., Prescott Valley, AZ (US); Geoff W. Habicht, Phoenix, AZ (US)

(73) Assignee: Ready Mix Naturals, LLC, Seguin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/799,650

(22) Filed: Aug. 9, 2024

(65) Prior Publication Data

US 2024/0400538 A1  Dec. 5, 2024

Related U.S. Application Data

(63) Continuation of application No. 18/593,597, filed on Mar. 1, 2024, which is a continuation of application No. 18/227,815, filed on Jul. 28, 2023, now Pat. No. 11,964,958.

(60) Provisional application No. 63/439,650, filed on Jan. 18, 2023.

(51) Int. Cl.
*C07D 401/04* (2006.01)
*A24B 15/167* (2020.01)
*A24B 15/30* (2006.01)

(52) U.S. Cl.
CPC .......... *C07D 401/04* (2013.01); *A24B 15/167* (2016.11); *A24B 15/301* (2013.01)

(58) Field of Classification Search
None
See application file for complete search history.

(56) References Cited

U.S. PATENT DOCUMENTS

| | | | | |
|---|---|---|---|---|
| 4,922,901 A | * | 5/1990 | Brooks | A61M 16/109 |
| | | | | 131/273 |
| 5,242,935 A | * | 9/1993 | Lippiello | A61P 25/00 |
| | | | | 514/343 |
| 6,041,789 A | | 3/2000 | Bankert et al. | |
| 10,973,255 B2 | | 4/2021 | Pandolfino | |
| 2003/0225142 A1 | * | 12/2003 | Crooks | C07D 401/04 |
| | | | | 546/276.4 |
| 2004/0123873 A1 | | 7/2004 | Calandro et al. | |
| 2013/0157995 A1 | | 6/2013 | Kem et al. | |
| 2013/0192620 A1 | | 8/2013 | Tucker et al. | |
| 2014/0190478 A1 | | 7/2014 | Liu | |
| 2014/0271946 A1 | * | 9/2014 | Kobal | A61K 31/201 |
| | | | | 562/598 |
| 2017/0189388 A1 | | 7/2017 | Arnold | |
| 2017/0325494 A1 | | 11/2017 | Cameron et al. | |
| 2018/0184704 A1 | | 7/2018 | Williams | |
| 2021/0112863 A1 | | 4/2021 | Hon | |
| 2021/0195938 A1 | | 7/2021 | Mua et al. | |
| 2023/0211907 A1 | | 7/2023 | Skeberg | |
| 2024/0245092 A1 | | 7/2024 | Owen et al. | |
| 2024/0270711 A1 | | 8/2024 | Owen et al. | |
| 2024/0350476 A1 | | 10/2024 | Tanakit et al. | |
| 2024/0400539 A1 | | 12/2024 | Owen et al. | |

FOREIGN PATENT DOCUMENTS

| | | |
|---|---|---|
| CN | 104473322 A | 4/2015 |
| CN | 114403494 A | 4/2022 |
| CN | 114437025 A | 5/2022 |
| WO | 2015148649 A1 | 10/2015 |
| WO | 2020205811 A1 | 10/2020 |
| WO | 2022053621 A1 | 3/2022 |

OTHER PUBLICATIONS

Pubchem, CID 129890930, Sep. 13, 2017, entire document, especially p. 2, compound listed.
Patent Cooperation Treaty, International Search Report & Written Opinion in Application No. PCT/US2023/029034, mailed Jan. 10, 2024.
United States Patent and Trademark Office, Restriction Requirement received in U.S. Appl. No. 18/227,815 dated Oct. 25, 2023.
United States Patent and Trademark Office, Non-Final Office Action received in U.S. Appl. No. 18/227,815 dated Dec. 1, 2023.
United States Patent and Trademark Office, Notice of Allowance received in U.S. Appl. No. 18/227,815 dated Mar. 22, 2024.
United States Patent and Trademark Office, Non-Final Office Action received in U.S. Appl. No. 18/593,597 dated Sep. 28, 2024.
Patent Cooperation Treaty (PCT), International Search Report and Written Opinion received in Application No. PCT/US2024/042756, Nov. 21, 2024.
Pogocki et al., Application of nicotine enantiomers, derivatives and analogues in therapy of neurodegenerative disorders, European Journal of Parmacology, 2007, 563, pp. 18-39, especially: p. 19, Fig. 1, formula nornicotine; p. 28, col. 1, para 1.

(Continued)

*Primary Examiner* — Dennis R Cordray

(74) *Attorney, Agent, or Firm* — SNELL & WILMER L.L.P.

(57) ABSTRACT

In various embodiments of the present disclosure, vaporizable alkaloid compositions are described that are capable of forming an inhalable vapor when dispensed from an electronic device such as an e-cigarette. The compositions herein comprise a substituted pyridine compound in combination with a chemosensory irritant, which in certain examples comprises a spice additive having a spiciness of from about 1,000 to about 20,000,000 Scoville Heat Units (SHU). A series of vaporizable alkaloid compositions having decreasing (w/v) amounts of substituted pyridine compound are provided as part of a smoking cessation program.

29 Claims, No Drawings

(56) References Cited

OTHER PUBLICATIONS

Liu et al., Analysis of nicotine and nicotine-related compounds in electronic cigarette liquids and aerosols by liquid chromatography-tandem mass spectrometry, Beitrage zur Tabakforschhung International/Contributions to Tobacco Research. 2017, vol. 27, No. 7, especially: p. 155, col. 2, para 2; p. 156, Figure 1, formula nicotine; p. 162, col. 1, para 1.

Hukkanen, et al., Metabolism and disposition kinetics of nicotine, Pharmacological Reviews. 2005. vol. 57, No. 1, pp. 79-115, entire document.

Owen, et al, Tobacco Harm Reduction and Pain Relief Products and Methods Thereof, U.S. Appl. No. 18/826,821, filed Sep. 6, 2024. (00300).

Owen, et al, Vaporizable Alkaloid Compositions and Methods of Use Thereof, U.S. Appl. No. 18/926,671, filed Oct. 25, 2024. (00717).

United States Patent and Trademark Office, Non-Final Office Action received in U.S. Appl. No. 18/807,086 dated Dec. 9, 2024.

Patent Cooperation Treaty, International Search Report & Written Opinion in Application No. PCT/US2024/045553, mailed Jan. 22, 2025.

Patent Cooperation Treaty, International Search Report & Written Opinion in Application No. PCT/US2024/052615, mailed Feb. 3, 2025.

Green et al. Nornicotine pretreatment decreases intravenous nicotine self-administration in rats Psychopharmacology. Aug. 19, 2000, vol. 152, p. 289-294 entire document.

United States Patent and Trademark Office, Notice of Allowance received in U.S. Appl. No. 18/593,597, dated Feb. 18, 2025.

The United States Patent and Trademark Office, Non-Final Office Action Received in U.S. Appl. No. 18/826,821, mailed Jun. 10, 2025.

Seeman, et al., "Nicotine Chemistry. The Addition of Alkyl Radicals to (S)-(-)-Nicotine: Synthesis of Optically Active 6-Alkylnicotines," Oct. 1985.

\* cited by examiner

VAPORIZABLE ALKALOID COMPOSITIONS AND METHODS OF USE THEREOF

CROSS-REFERENCE TO RELATED APPLICATIONS

This application is a continuation of U.S. patent application Ser. No. 18/593,597, filed Mar. 1, 2024 entitled "Vaporizable Alkaloid Compositions and Methods of Use Thereof," which is a continuation of U.S. patent application Ser. No. 18/227,815, filed on Jul. 28, 2023, now U.S. Pat. No. 11,964,958, issued Apr. 23, 2024, entitled "Vaporizable Alkaloid Compositions and Methods of Use Thereof" which claims priority to, and the benefit of, U.S. Provisional Patent Application Ser. No. 63/439,650 filed Jan. 18, 2023 and entitled "Vaping Liquid With Analogs For Vaping Devices," the disclosure of which is incorporated herein by reference in its entirety for all purposes.

FIELD

The present disclosure generally relates to vaporizable and inhalable compositions comprising both physiologically and sensory active substances, and in particular to vaporizable compositions comprising one or more substituted pyridine compounds, or salts thereof, or mixed salts thereof.

BACKGROUND

It is common knowledge that smokers can experience health benefits from cigarette cessation, and in general, most adult smokers in the U.S. express a desire to quit smoking. Electronic Nicotine Delivery Systems (ENDS), depending on the composition of the vaporizable liquid, should, at least in principle, provide a viable cessation aid to smoking. However, various studies have suggested that users of electronic devices to self-administer nicotine are actually not more likely to quit smoking tobacco products. See, for example, B. Kaplan, et al., "Effectiveness of ENDS, NRT and Medication for Smoking Cessation Among Cigarette-Only Users," *Tob Control* 2023; 32:302-307 and R. El Dib, et al., "Electronic Nicotine Delivery Systems and/or Electronic Non-Nicotine Delivery Systems for Tobacco Smoking Cessation or Reduction: A Systematic Review and Meta-Analysis," *BMJ Open* 2017; 7: e012680.

Complete substitution of an electronically administered vapor for actual tobacco smoking requires compliance, much like patient compliance to a pharmaceutical subscription. In the case of a smoker, compliance with an electronic device relies on having identical or at least close to identical sensory effects delivered electronically from a vaporizable composition as would be experienced from inhaling tobacco smoke from a burning cigarette. To date and evidenced by the data showing a lack of cessation, this has not been accomplished in the industry.

Therefore, new vaporizable compositions are needed that can provide an acceptable personal experience to a previous tobacco smoker when vaporized through an electronic device and inhaled.

SUMMARY

It has now been surprisingly discovered that vaporizable compositions can be optimized to provide a balance between senses when vaporized and inhaled, so as to simulate as closely as possible, the sensory experience an individual has when smoking traditional tobacco products.

In accordance with the present disclosure, novel vaporizable alkaloid compositions and methods of compounding are provided. In general, compositions herein are optimized to aid compliance to a smoking cessation program by providing smokers with a viable and complete alternative to tobacco smoking.

In various embodiments, a vaporizable alkaloid composition herein comprises at least one substituted pyridine compound, or salt thereof, or mixed salt thereof; at least one chemosensory irritant; at least one solvent; and optionally, at least one flavoring agent, wherein the vaporizable alkaloid composition is entirely devoid of nicotine.

In various embodiments, a vaporizable alkaloid composition comprises:
at least one substituted pyridine compound of Formula (I), or salt or mixed salt thereof;

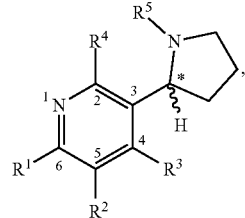

(I)

wherein $R^1$, $R^2$, $R^3$, $R^4$, and $R^5$ are independently selected from H, alkyl, substituted alkyl, cycloalkyl, substituted cycloalkyl, alkenyl, and substituted alkenyl, with the proviso that if $R^5$ is $CH_3$, then $R^1$, $R^2$, $R^3$, and $R^4$ cannot all be H;
at least one chemosensory irritant;
at least one solvent; and
optionally, at least one flavoring agent,
wherein the vaporizable alkaloid composition is entirely devoid of (R) or (S) nicotine.

In various embodiments, $R^5$ is $CH_3$ and at least one of $R^1$, $R^2$, $R^3$, and $R^4$ is not H.

In various embodiments, $R^5$ is $-(CH_2)n-NR^6R^7$, wherein n is an integer from 1 to 10, and wherein $R^6$ and $R^7$ are independently selected from H, alkyl, substituted alkyl, cycloalkyl, substituted cycloalkyl, alkenyl and substituted alkenyl, or $R^6$ and $R^7$ together with the N atom to which they are bonded form a 3-8 membered optionally substituted heterocyclic ring.

In various embodiments, $R^5$ is H, and at least one of $R^1$, $R^2$, $R^3$, and $R^4$ is $-(CH_2)n-NR^6R^7$, wherein n is an integer from 1 to 10, and wherein $R^6$ and $R^7$ are independently selected from H, alkyl, substituted alkyl, cycloalkyl, substituted cycloalkyl, alkenyl and substituted alkenyl, or $R^6$ and $R^7$ together with the N atom to which they are bonded form a 3-8 membered optionally substituted heterocyclic ring.

In various embodiments, the substituted pyridine compound, or salt thereof, or mixed salt thereof, is selected from (R) or (S)-3-(pyrrolidin-2-yl)pyridine, (R) or (S)-2-methyl-3-(1-methylpyrrolidin-2-yl)pyridine, (R) or (S)-4-methyl-3-(1-methylpyrrolidin-2-yl)pyridine, (R) or (S)-3-methyl-5-(1-methylpyrrolidin-2-yl)pyridine, (R) or (S)-2-methyl-5-(1-methylpyrrolidin-2-yl)pyridine, (R) or (S)-2,6-dimethyl-3-(1-methylpyrrolidin-2-yl)pyridine, (R) or (S)-2,4-dimethyl-5-(1-methylpyrrolidin-2-yl)pyridine, (R) or (S)-2,3-dimethyl-5-(1-methylpyrrolidin-2-yl)pyridine, (R) or (S)-2,4-dimethyl-3-(1-methylpyrrolidin-2-yl)pyridine, (R) or (S)-2,5-dimethyl-3-(1-methylpyrrolidin-2-yl)pyridine, (R)

or (S)-3,4-dimethyl-5-(1-methylpyrrolidin-2-yl)pyridine, (R) or (S)-1-(2-aminoethyl)-2-(3-pyridyl)pyrrolidine, (R) or (S)-1-(3-aminopropyl)-2-(3-pyridyl)pyrrolidine, (R) or (S)-1-(4-aminobutyl)-2-(3-pyridyl)pyrrolidine, (R) or (S)-1-(5-aminopentyl)-2-(3-pyridyl)pyrrolidine, (R) or (S)-1-(2-dimethylaminoethyl)-2-(3-pyridyl)pyrrolidine, (R) or (S)-1-(3-dimethylaminopropyl)-2-(3-pyridyl)pyrrolidine, (R) or (S)-1-(4-dimethylaminobutyl)-2-(3-pyridyl)pyrrolidine, (R) or (S)-3-(2-(6-methylpyridin-3-yl)pyrrolidin-1-yl)propanenitrile, (R) or (S)-4-(2-(6-methylpyridin-3-yl)pyrrolidin-1-yl)butanenitrile, (R) or (S)-1-(3-aminopropyl)-2-(6-methyl-3-pyridyl)pyrrolidine, (R) or (S)-1-[3-(N,N-dimethylamino)propyl]-2-(6-methyl-3-pyridyl)pyrrolidine, (R) or (S)-1-(N,N-diethyl-3-aminopropyl-2-(3-pyridyl)pyrrolidine, (R) or (S)-3-(1-(2-(pyrrolidin-1-yl)ethyl)pyrrolidin-2-yl)pyridine, (R) or (S)-3-(1-(2-(piperidin-1-yl)ethyl)pyrrolidin-2-yl)pyridine, (R) or (S)-4-(2-(2-(pyridin-3-yl)pyrrolidin-1-yl)ethyl)morpholine, (R) or (S)-3-(1-(3-(pyrrolidin-1-yl)propyl)pyrrolidin-2-yl)pyridine, (R) or (S)-3-(1-(3-(piperidin-1-yl)propyl)pyrrolidin-2-yl)pyridine, and (R) or (S)-4-(3-(2-(pyridin-3-yl)pyrrolidin-1-yl)propyl)morpholine.

In various embodiments, the substituted pyridine compound, or salt thereof, or mixed salt thereof, is (S)-2-methyl-5-(1-methylpyrrolidin-2-yl)pyridine.

In various embodiments, the substituted pyridine compound or salt or mixed salt thereof is selected from (2S)-1-methyl-2-(6-methylpyridin-3-yl)pyrrolidin-1-ium acetate, (2S)-1-methyl-2-(6-methylpyridin-3-yl)pyrrolidin-1-ium citrate, or mixtures thereof.

In various embodiments, the chemosensory irritant is selected from the group consisting of oleocanthal, 4-hydroxy-2-nonenal, 4-oxo-2-nonenal, allicin, allyl isothiocyanate, icilin, polygodial, cinnamaldehyde, trans-p-methoxycinnamaldehyde, methyl syringate, 2-chlorobenzylidene malononitrile, 1-chloroacetophenone, ethyl bromoacetate, 4-hydroxyhexenal, toluene diisocyanate, p-benzoquinone, methyl p-hydroxybenzoate, flufenamic acid, niflumic acid, mefenamic acid, diclofenac, hydroxy-α-sanshool, 6-paradol, linalool, carvacrol, eugenol, thymol, vanillin, methyl eugenol, 2,6-dimethylphenol, 2,5-dimethylphenol, 3,4-dimethylphenol, 2,6-diisopropylphenol, caffeine, farnesyl thiosalicylic acid, 4-allylanisole, curcumin, niacin, camphor, olvanil, arvanil, anandamide, cannabidiol, $\Delta^9$-tetrahydrocannabinol, baicalein, baicalin, wogonin, norwogonin, oroxylin A, β-sitosterol and mixtures thereof.

In various embodiments, the at least one substituted pyridine compound of Formula (I), or salt thereof, or mixed salt thereof, consists of a mixture of (S)-2-methyl-3-(1-methylpyrrolidin-2-yl)pyridine free base and (2S)-1-methyl-2-(6-methylpyridin-3-yl)pyrrolidin-1-ium citrate/acetate mixed salts.

In various embodiments, the chemosensory irritant is a spice additive exhibiting a spiciness of from about 1,000 to about 20,000,000 Scoville Heat Units (SHU).

In various embodiments, the spice additive is selected from the group consisting of capsaicin, dihydrocapsaicin, norcapsaicin, nordihydrocapsaicin, homocapsaicin, homodihydrocapsaicin, gingerol, piperine, Shogaol, isopiperine, chavicine, isochavicine, 2-piperamine, piperanine (4,5-dihydropiperine), piperamide, 4-pipericide, piperyline, piperlonguminine, piperettine, piperdardine (6,7-dihydropiperettine), 5-sarmentodine, 6-sarmentine, 7-trichostachine, and mixtures thereof.

In various embodiments, the spice additive is capsaicin or a mixture of capsaicinoids.

In various embodiments, the solvent is selected from the group consisting of propylene glycol, water, ethanol, glycerin, and mixtures thereof.

In various embodiments, vaporizable alkaloid compositions further include an organic acid selected from the group consisting of formic acid, acetic acid, trifluoroacetic acid, aspartic acid, butanoic acid, butyric acid, 2-methylbutyric acid, 3-methylbutyric acid, benzoic acid, caprylic acid, citric acid, crotonic acid, ethylenediaminetetraacetic acid, fumaric acid, gluconic acid, glutamic acid, glyceric acid, glycolic acid, lactic acid, lauric acid, levulinic acid, maleic acid, malic acid, malonic acid, mandelic acid, methane sulfonic acid, oxalic acid, phenylacetic acid, phthalic acid, picric acid, propionic acid, pyruvic acid, salicylic acid, stearic acid, succinic acid, tannic acid, tartaric acid, tartronic acid, valeric acid, and mixtures thereof.

In various embodiments, the organic acid is selected from the group consisting of citric acid, acetic acid, benzoic acid, tartaric acid, lactic acid, salicylic acid, malic acid, levulinic acid, and mixtures thereof.

In various embodiments, the molar ratio of total substituted pyridine compound to total organic acid is about 25:1 to about 75:1.

In various embodiments, a vaporizable alkaloid composition comprises:
from about 1 wt. % to about 80 wt. % of a substituted pyridine compound, or salt, or mixed salt thereof, according to Formula (I):

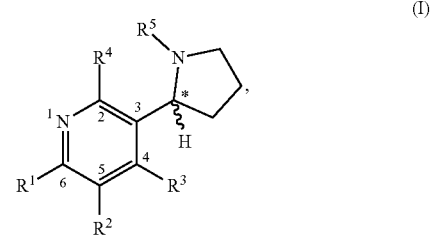

wherein $R^1$, $R^2$, $R^3$, $R^4$, and $R^5$ are independently selected from H, alkyl, substituted alkyl, cycloalkyl, substituted cycloalkyl, alkenyl, and substituted alkenyl, with the proviso that if $R^5$ is $CH_3$, then $R^1$, $R^2$, $R^3$, and $R^4$ cannot all be H;
from about 0.05 wt. % to about 1.5 wt. % in total of at least one organic acid;
from about 0.0001 wt. % to about 0.50 wt. % of a spice additive having a spiciness of from about 1,000 to about 20,000,000 Scoville Heat Units (SHU); and
remainder solvent,
wherein the weight percentages are based on the total weight of the vaporizable alkaloid composition; and
wherein the molar ratio of moles of substituted pyridine compound to the total moles of organic acid is about 25:1 to about 75:1.

In various embodiments, the substituted pyridine compound is (S)-2-methyl-5-(1-methylpyrrolidin-2-yl)pyridine.

In various embodiments, the molar ratio of moles of (S)-2-methyl-5-(1-methylpyrrolidin-2-yl)pyridine to the total moles of organic acid is about 50:1.

In various embodiments, the (w/v) concentration of (S)-2-methyl-5-(1-methylpyrrolidin-2-yl)pyridine in the vaporizable alkaloid composition is from about 1 mg/mL to about 1,000 mg/mL.

In various embodiments, the (w/v) concentration of (S)-2-methyl-5-(1-methylpyrrolidin-2-yl)pyridine in the vaporizable alkaloid composition is about 100 mg/mL.

In various embodiments, the at least one organic acid consists of a mixture of citric acid and acetic acid.

In various embodiments, the spice additive comprises capsaicin.

In various embodiments, the solvent is selected from the group consisting of propylene glycol, glycerin, ethanol, and mixtures thereof.

In various embodiments, a method of manufacturing a vaporizable alkaloid composition comprises:
preparing a first premix comprising of a chemosensory irritant and at least one organic acid dissolved in a suitable solvent or solvent mixture;
preparing a second premix comprising at least one substituted pyridine compound dissolved in a suitable solvent or solvent mixture, said substituted pyridine compound having a structure of Formula (I):

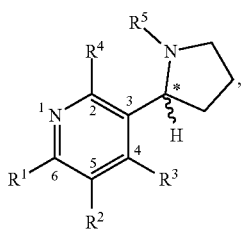

or salt thereof, or mixed salt thereof, wherein $R^1$, $R^2$, $R^3$, $R^4$, and $R^5$ are independently selected from H, alkyl, substituted alkyl, cycloalkyl, substituted cycloalkyl, alkenyl, and substituted alkenyl, with the proviso that if $R^5$ is $CH_3$, then $R^1$, $R^2$, $R^3$, and $R^4$ cannot all be H;
combining first and second premixes; and
optionally heating the resulting mixture until the resulting mixture becomes optically clear, thus producing the vaporizable alkaloid composition.

In various embodiments, the first premix comprises capsaicin or a mixture of capsaicinoids, acetic acid, and citric acid dissolved in a mixture of propylene glycol and ethanol, and wherein the second premix comprises (S)-2-methyl-5-(1-methylpyrrolidin-2-yl)pyridine dissolved in glycerin.

In various embodiments, a method for promoting smoking cessation in an individual desirous of cessation comprises:
administering to the individual, over a time period determined for cessation, a series of vaporizable alkaloid compositions for the individual to inhale by vaping, each vaporizable alkaloid composition in the series comprising at least one substituted pyridine compound, or salt or mixed salt thereof, having Formula (I):

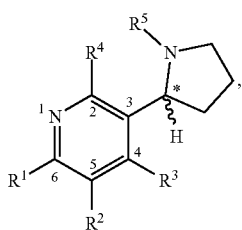

wherein $R^1$, $R^2$, $R^3$, $R^4$, and $R^5$ are independently selected from H, alkyl, substituted alkyl, cycloalkyl, substituted cycloalkyl, alkenyl, and substituted alkenyl, with the proviso that if $R^5$ is $CH_3$, then $R^1$, $R^2$, $R^3$, and $R^4$ cannot all be H;
wherein each of the vaporizable alkaloid compositions in the series comprises a decreasing (w/v) amount of said substituted pyridine compound, or salt, or mixed salt thereof; and
wherein the individual inhales by vaping each composition in the series beginning with the composition having the highest level (w/v) of said substituted pyridine compound, or salt, or mixed salt thereof, and ending the time period determined for cessation with the composition having the lowest level (w/v) of said substituted pyridine compound, or salt, or mixed salt thereof, such that at the end of the time period determined for cessation the individual ceases smoking.

In various embodiments, each vaporizable alkaloid composition in the series of vaporizable alkaloid compositions comprises (S)-2-methyl-5-(1-methylpyrrolidin-2-yl)pyridine or salt, or mixed salt thereof.

In various embodiments, the vaporizable alkaloid composition in the series of vaporizable alkaloid compositions having the highest level (w/v) of said substituted pyridine compound, or salt, or mixed salt thereof comprises about 100 mg/mL (S)-2-methyl-5-(1-methylpyrrolidin-2-yl)pyridine.

In various embodiments, the vaporizable alkaloid composition in the series of vaporizable alkaloid compositions having the lowest level (w/v) of said substituted pyridine compound, or salt, or mixed salt thereof comprises no more than about 1 mg/mL (S)-2-methyl-5-(1-methylpyrrolidin-2-yl)pyridine.

In various embodiments, the time period determined for cessation is part of a smoking cessation program that further includes dispensation of the series of vaporizable alkaloid compositions to the individual desirous of cessation over the time period determined for cessation.

In various embodiments, an alkaloid dispensing pouch adapted for release of an alkaloid therefrom into the oral cavity of an individual comprises:
a saliva-permeable nonwoven fabric defining an enclosure containing an alkaloid composition filled therein, said alkaloid composition comprising:
at least one substituted pyridine compound, or salt, or mixed salt thereof, according to Formula (I):

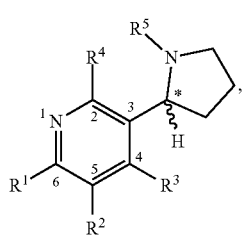

wherein $R^1$, $R^2$, $R^3$, $R^4$, and $R^5$ are independently selected from H, alkyl, substituted alkyl, cycloalkyl, substituted cycloalkyl, alkenyl, and substituted alkenyl, with the proviso that if $R^5$ is $CH_3$, then $R^1$, $R^2$, $R^3$, and $R^4$ cannot all be H; and
a carrier,
wherein the alkaloid dispensing pouch is entirely devoid of devoid of (R) or (S) nicotine.

In various embodiments, the alkaloid composition comprises an admixture of said substituted pyridine compound of Formula (I) and the carrier.

In various embodiments, the carrier comprises microcrystalline cellulose.

In various embodiments, the alkaloid composition further comprises a solvent, wherein the alkaloid composition consists of a liquid composition adsorbed onto the carrier.

In various embodiments, the alkaloid composition further comprises a chemosensory irritant. In various embodiments, the chemosensory irritant comprises a spice having a spiciness of from about 1,000 SHU to about 20,000,000 SHU.

In various embodiments, an alkaloid dispensing pouch adapted for release of an alkaloid therefrom into the oral cavity of an individual comprises a saliva-permeable nonwoven fabric defining an enclosure containing an alkaloid composition filled therein, said alkaloid composition comprising a vaporizable alkaloid composition further comprising at least one substituted pyridine compound of Formula (I), or salt or mixed salt thereof;

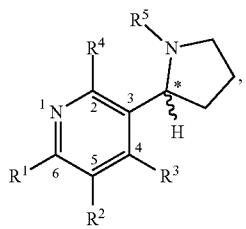

(I)

wherein $R^1$, $R^2$, $R^3$, $R^4$, and $R^5$ are independently selected from H, alkyl, substituted alkyl, cycloalkyl, substituted cycloalkyl, alkenyl, and substituted alkenyl, with the proviso that if $R^5$ is $CH_3$, then $R^1$, $R^2$, $R^3$, and $R^4$ cannot all be H; at least one chemosensory irritant; at least one solvent; and optionally, at least one flavoring agent, wherein the vaporizable alkaloid composition is entirely devoid of (R) or (S) nicotine; and wherein the vaporizable alkaloid composition is adsorbed on a carrier.

In various embodiments, the vaporizable alkaloid composition comprises (S)-2-methyl-5-(1-methylpyrrolidin-2-yl)pyridine, citric acid and acetic acid.

In various embodiments, the carrier comprises microcrystalline cellulose.

In various embodiments, the chemosensory irritant comprises capsaicin or a mixture of capsaicinoids.

In various embodiments, the solvent is selected from the group consisting of propylene glycol, water, ethanol, glycerin, and mixtures thereof.

DETAILED DESCRIPTION

The detailed description of exemplary embodiments makes reference to the accompanying drawings, which show exemplary embodiments by way of illustration and their best mode. While these exemplary embodiments are described in sufficient detail to enable those skilled in the art to practice the invention, it should be understood that other embodiments may be realized and that logical, chemical, and mechanical changes may be made without departing from the spirit and scope of the inventions. Thus, the detailed description is presented for purposes of illustration only and not of limitation. For example, unless otherwise noted, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

In various embodiments of the present disclosure, novel vaporizable alkaloid compositions are disclosed. Compositions herein are optimized to provide a balance between nasal, throat, and head senses when vaporized and inhaled, so as to simulate as closely as possible the same sensory experience an individual has when smoking traditional tobacco products. In general, compositions herein are optimized to aid compliance to a smoking cessation program. In various embodiments herein, tobacco smokers are provided with a viable and complete alternative to smoking.

In various embodiments, a vaporizable alkaloid composition herein comprises:
  at least one substituted pyridine compound, or salt, or mixed salt thereof;
  at least one chemosensory irritant;
  at least one solvent; and
  optionally, at least one flavoring agent, wherein the vaporizable alkaloid composition is entirely devoid of nicotine.

In certain examples, the compositions provided herein may be diluted prior to vaporization and inhalation, such as by a third party manufacturer or by an end user of a refillable electronic device, with an appropriate solvent or mixture of solvents such as vegetable glycerin and/or propylene glycol, to provide custom inhalable compositions having lesser amounts of substituted pyridine compound and spice additive than the beginning composition. In preferred examples, a third party will design and conduct a smoking cessation program for an individual in combination with providing vaping liquids having progressively lesser amounts of substituted pyridine compound and spice additive over the course of the program. In this way, a consumer can comply with a smoking cessation program and use vaping liquids having lesser and lesser amounts of substituted pyridine compound and spice additive over time, until the user is essentially inhaling vaporized solvent with no other discernible materials except perhaps flavoring agents.

Definitions and Interpretations

Unless defined otherwise, all technical and scientific terms used herein have the same meaning as commonly understood by those of ordinary skill in the chemical arts and medicinal chemistry arts to which this disclosure relates. Although any methods and materials similar or equivalent to those described herein can be used in the practice or testing of the subject matter of the present disclosure, preferred methods and materials are described. As per common practice in organic chemistry, chemical structures having a chiral center either illustrated with wavy bonds thereon or not illustrated three dimensionally with wedged or dashed bonds, or not labeled (R) or (S) adjacent to the chiral center or in the corresponding structural name, is assumed to represent both enantiomers. Similarly, chemical structures having multiple chiral centers not presented three dimensionally or labeled as having particular chirality are assumed to include all possible stereoisomers. Compounds of the present disclosure comprise any physiochemical or stereochemical form they may possibly assume, such as, for example, isomers, prodrugs, active metabolites, tautomers, stereoisomers, regioisomers, solvated forms, salts, and polymorphic forms. Amorphous forms lack a distinguishable crystal lattice and therefore lack an orderly arrangement of structural units. Many alkaloids have amorphous forms, crystalline forms, or mixtures thereof. Methods of generating such chemical forms are known to one skilled in the art, in addition to the crystallographic methods to determine extent and type of crystallinity.

Compositions of the present disclosure comprise alkaloids that may be protonated by acids also present in the compositions, and thus at least partly or even entirely in the form of a salt in the various compositions. Salts of alkaloids include any salt derived from an inorganic or organic acid preferably an organic acid or mixtures thereof. Examples of inorganic salts include but are not limited to, salts of hydrobromic acid, hydrochloric acid, nitric acid, phosphoric acid and sulfuric acid. Examples of organic acid salts include, for example, salts of formic acid, acetic acid, trifluoroacetic acid, aspartic acid, butanoic acid, butyric acid, 2-methylbutyric acid, 3-methylbutyric acid, benzoic acid, caprylic acid, citric acid, crotonic acid, ethylenediaminetetraacetic acid (EDTA), fumaric acid, gluconic acid, glutamic acid, glyceric acid, glycolic acid, lactic acid, lauric acid, levulinic acid, maleic acid, malic acid, malonic acid, mandelic acid, methane sulfonic acid, oxalic acid, phenylacetic acid, phthalic acid, picric acid, propionic acid, pyruvic acid, salicylic acid, stearic acid, succinic acid, tannic acid, tartaric acid, tartronic acid, valeric acid, and any combinations thereof, or any other such acid presently known or yet to be discovered or synthesized. Such alkaloid salts can be prepared by reaction of an alkaloid free base compound with a suitable acid or mixture of acids in a manner known by those skilled in the art. When mixed acids are reacted with the alkaloids disclosed herein to make alkaloid salts, no attempt is made to quantify the resulting mole percentages of each individual alkaloid salt, but rather the resulting alkaloid salts are referred to as "mixed salts."

As used herein, the term "alkyl" refers to linear or branched monovalent saturated hydrocarbon substituents, optionally substituted with one or more functional groups anywhere on or within the substituent. Unless otherwise specified, an alkyl group may contain any number of carbon atoms, such as for example, $C_1$-$C_{24}$, $C_1$-$C_{18}$, $C_1$-$C_{10}$, $C_1$-$C_8$, or $C_1$-$C_6$. Examples of alkyl substituents include, but are not limited to, methyl, ethyl, n-propyl, isopropyl, n-butyl, isobutyl, sec-butyl, tert-butyl, n-pentyl, iso-pentyl neo-pentyl, n-hexyl, iso-hexyl, octadecyl, dodecyl, and so forth. An alkyl substituent herein may be substituted, i.e., having one or more substituent groups appended on the alkyl group or incorporated within the alkyl chain. A substitution within the alkyl substituent chain may comprise an ether, sulfide, amino, or imine linkage, i.e., —O—, —S—, —N(R')—, or —N=, for example, or some other intervening heteroatom(s). Examples of substitution on an alkyl substituent include, but are not limited to, —CN, —N$_3$, —NH$_2$, —NHR', —N(R')$_2$, —NO$_2$, —NH—NH$_2$, —NH—NHR', —NH—NR'$_2$, -halo, —SH, —SR', —S(=O)R', —SO$_2$R', —OPO$_3^{2-}$, —PO$_3^{2-}$, —OH, —OR', —C(=O)R', —OC(=O)R', —CO$_2$R', —NHC(=O)R', —NR'C(=O)R', —C(=O)NHR', —C(=O)NR'$_2$, alkyl, alkenyl, cycloalkyl, heterocyclyl, and aryl, wherein each R' above is independently selected from hydrogen —H and an alkyl moiety, including, for example, $C_{1-6}$ alkyl (e.g., —CH$_3$, —C$_2$H$_5$, -isopropyl, -tert-butyl, etc.), $C_{1-6}$ alkoxy (e.g., —OCH$_3$, —OC$_2$H$_5$), halogenated $C_{1-6}$ alkyl (e.g., —CF$_3$, —CHF$_2$, —CH$_2$F), and halogenated $C_{1-6}$ alkoxy (e.g., —OCF$_3$, —OC$_2$F$_5$). In various examples, two R' substituents in any of these functional groups may form a ring structure.

As used herein, the term "cycloalkyl" includes any 3-, 4-, 5-, 6-, 7-, or 8-membered, saturated or unsaturated, non-aromatic carbocyclic ring, optionally substituted with one or more functional groups at any location on the cyclic substituent. Examples of cycloalkyl groups include, but are not limited to, cyclopropyl, cyclobutyl, cyclopentyl, 1-, 2-, or 5-cyclopentadienyl, cyclohexyl, 1-, 3- or 4-cyclohexenyl, 1-, 2-, or 5-(1,3-cyclohexadienyl), 1- or 3-(1,4-cyclohexadienyl), cycloheptyl, 1-, 3-, 4-, or 5-cycloheptenyl, cyclooctanyl, and so forth. Examples of substitution on an cycloalkyl substituent include, but are not limited to, —CN, —N$_3$, —NH$_2$, —NHR', —N(R')$_2$, —NO$_2$, —NH—NH$_2$, —NH—NHR', —NH—NR'$_2$, -halo, —SH, —SR', —S(=O)R', —SO$_2$R', —OPO$_3^{2-}$, —PO$_3^{2-}$, —OH, —OR', —C(=O)R', —OC(=O)R', —CO$_2$R', —NHC(=O)R', —NR'C(=O)R', —C(=O)NHR', —C(=O)NR'$_2$, alkyl, alkenyl, cycloalkyl, heterocyclyl, and aryl, wherein each R' above is independently selected from —H and an alkyl moiety, including, for example, $C_{1-6}$ alkyl (e.g., —CH$_3$, —C$_2$H$_5$, -isopropyl, -tert-butyl, etc.), $C_{1-6}$ alkoxy (e.g., —OCH$_3$, —OC$_2$H$_5$), halogenated $C_{1-6}$ alkyl (e.g., —CF$_3$, —CHF$_2$, —CH$_2$F), and halogenated $C_{1-6}$ alkoxy (e.g., —OCF$_3$, —OC$_2$F$_5$).

As used herein, the term "alkenyl" refers to linear or branched monovalent or divalent unsaturated hydrocarbon substituents, optionally substituted with one or more functional groups anywhere on or within the substituent. An alkenyl substituent can be viewed as being divalent if the sp$^2$ carbon is part of a molecule bearing the alkenyl substituent. An illustrative example is methylenecyclohexane, which can be viewed as cyclohexane substituted with a methylene group (i.e., a divalent alkenyl substituent, =CH$_2$). Unless otherwise specified, an alkenyl group may contain any number of carbon atoms, such as for example, $C_1$-$C_{24}$, $C_1$-$C_{18}$, $C_1$-$C_{10}$, $C_1$-$C_8$, or $C_1$-$C_6$, and any degrees of unsaturation. Examples of alkenyl substituents include, but are not limited to, methylene/methylidine (=CH$_2$), ethylene/ethenyl (—CH=CH$_2$ or =CH—CH$_3$), propylene/propenyl (—CH$_2$—CH=CH$_2$, cis or trans —CH=CH—CH$_3$, =C(CH$_3$)$_2$, or cis or trans =CH—CH$_2$CH$_3$), and so forth. An alkenyl substituent herein may be substituted, i.e., having one or more substituent groups appended on the alkenyl group or incorporated within the alkenyl chain. A substitution within the alkenyl substituent may comprise an ether, sulfide, amino, or imine linkage, i.e., —O—, —S—, —N(R')—, or —N=, for example, or some other intervening heteroatom(s). Examples of substitution on an alkenyl substituent include, but are not limited to, —CN, —N$_3$, —NH$_2$, —NHR', —N(R')$_2$, —NO$_2$, —NH—NH$_2$, —NH—NHR', —NH—NR'$_2$, -halo, —SH, —SR', —S(=O)R', —SO$_2$R', —OPO$_3^{2-}$, —PO$_3^{2-}$, —OH, —OR', —C(=O)R', —OC(=O)R', —CO$_2$R', —NHC(=O)R', —NR'C(=O)R', —C(=O)NHR', —C(=O)NR'$_2$, alkyl, alkenyl, cycloalkyl, heterocyclyl, and aryl, wherein each R' above is independently selected from an alkyl moiety, including, for example, $C_{1-6}$ alkyl (e.g., —CH$_3$, —C$_2$H$_5$, -isopropyl, -tert-butyl, etc.), $C_{1-6}$ alkoxy (e.g., —OCH$_3$, —OC$_2$H$_5$), halogenated $C_{1-6}$ alkyl (e.g., —CF$_3$, —CHF$_2$, —CH$_2$F), and halogenated $C_{1-6}$ alkoxy (e.g., —OCF$_3$, —OC$_2$F$_5$). In various examples, two R' substituents in any of these functional groups may form a ring structure.

As used herein, the term "propylene glycol" or more simply "PG" refers to propane-1,2-diol (α-propylene glycol) and not the 1,3-diol isomer, unless indicated otherwise.

Further, the propylene glycol used herein comprises a racemic mixture of isomers, unless indicated otherwise, and is typically produced on a global industrial scale by hydrolysis of propylene oxide. PG is generally the ingredient recognized in vaporizable compositions as being responsible for the white cloud of vapor seen in vaping.

As used herein, the term "vegetable glycerin" or more simply "VG" takes on its ordinary meaning in organic chemistry and food science, which is $HOCH_2$—$CH(OH)$—$CH_2OH$, having been derived from triglyceride of vegetable origin.

As used herein, the term "inhalable" refers to a characteristic of vaporizable alkaloid compositions in accordance with the present disclosure, namely that the compositions are suitable for inhalation by a user. The inhalable alkaloid compositions disclosed herein are vaporizable and thus suitable for use in an electronic cigarette device, meaning that they can be vaporized by the heating element within such electronic devices, thereby allowing inhalation by a user in a practice called "vaping." Stated another way, vaporizable alkaloid compositions herein are inhalable compositions. Unless otherwise specified, the phrase "the inhalable composition" or "the inhalable compositions" refers to the vaporizable alkaloid compositions in accordance with the present disclosure.

As used herein, the terms "e-cigarette" or "ENDS" (electronic nicotine delivery system) refer generally to any electronic device capable of vaporizing a liquid composition into a vapor that can be inhaled by an individual using the device. So as not to be limiting, an "e-cigarette" herein means any design, such as a cigar, a vape pen, or any other electronic device, refillable or disposable, having a reservoir containing a vaporizable liquid therein and having the capability of vaporizing the vaporizable liquid. For simplicity, the term "electronic device" may be used to refer to any and all refillable and disposable instruments for vaping.

As used herein, the term "throat hit" refers to a sensory effect experienced at the back of the throat, perceived by an individual inhaling a vapor, such as vapor obtained from a burning cigarette or vapor delivered from an electronic device like an e-cigarette capable of vaporizing a liquid composition. Throat hit is a type of irritating "bite" experienced at the back of the throat, which prior to the development of e-cigarettes was something not only experienced by smokers but also anticipated and enjoyed by smokers. Although subjective rather than objective, throat hit can be quantified through the use of sensory panels where participants in the panel rank the perceived throat hit on a scale of 1-10, for example, or compare throat hit between e-cigarette products and/or for an e-cigarette product relative to traditional cigarettes. In some examples, throat hit may be quantified as being less than, equal to, or more than the throat hit experienced from a particular cigarette in comparison. An exemplary cigarette used to standardize throat hit, such as in a sensory panel where participants rank throat hit, is Marlboro® Filter Cigarettes, Gold Pack 100's, available from Phillips IGA. As explained herein, throat hit can generally be achieved in an individual by inclusion of a chemosensory irritant in the vaporizable alkaloid compositions of the present disclosure, and particularly by use of a spice additive as the chemosensory irritant.

As used herein, the term "vaping" refers to the act of using an e-cigarette or other ENDS device to inhale a vapor generated electronically from the vaporization of a liquid composition. Vaping is seen as a similar endeavor to smoking tobacco products, recognizing that an e-cigarette and vaping is not limited to nicotine. Vaping may include personal inhalation of cannabinoids, nicotine analogs, other physiologically active substances, flavorings, etc.

As used herein, the term "vape juice" or "e-juice" refers to a liquid composition capable of vaporization in an e-cigarette or other ENDS device to produce a vapor that can be inhaled by an individual who is vaping. In various embodiments herein, vape juice compositions are described, and which in certain examples comprise vaporizable alkaloid compositions and dilutions therefrom.

As used herein, the term "cloud" refers to the white vapor visible when a vape juice is vaporized by an e-cigarette or other ENDS device, inhaled and then exhaled. As discussed herein, a cloud is an important attribute to a successful vape juice because it is a feature that a person vaping looks for. Although subjective rather than objective, the appearance of a cloud can be quantified through the use of sensory panels where participants in the panel rank appearance of a cloud while vaping on a scale of 1-10, for example, or compare a visible cloud between e-cigarette products and/or relative to what is seen in the air when smoking traditional burning cigarettes. In some examples, a cloud may be quantified as being less than, equal to, or more than the cloud seen when smoking a particular cigarette in comparison. An exemplary cigarette used to standardize the appearance of a cloud, such as in a sensory panel where participants rank appearance of a cloud, is Marlboro® Filter Cigarettes, Gold Pack 100's, available from Phillips IGA.

As used herein, the term "head rush" refers to the light-headedness experienced by tobacco smokers and vapers that inhale nicotine, nicotine analog, THC and other products that contain a physiologically active substance. Smokers have described this sensory experience as a ringing sensation in their heads, or a rush of adrenaline. The sensory effect is believed to be caused by nicotine or other drug in the blood and brain triggering release of adrenaline that in turn causes a tightening of the blood vessels and a temporary rise in heart rate and blood pressure of the person inhaling the active substance. This sensory experience is personal, and it varies between drug actives and between individuals because of variances in physiological tolerance. A head rush might appear within 10 seconds of inhaling nicotine, and it might last as long as 10-30 minutes. However, as a smoker or vaper continues smoking or vaping, they become more tolerant and the head rush regularly experienced becomes shorter-lasting over time. Although subjective rather than objective, head rush can be quantified through the use of sensory panels where participants in the panel rank the perceived head rush on a scale of 1-10, for example, or compare the perceived head rush between e-cigarette products and/or for an e-cigarette product relative to traditional cigarettes. In some examples, head rush may be quantified as being less than, equal to, or more than the head rush experienced from a particular cigarette in comparison. An exemplary cigarette used to standardize throat hit, such as in a sensory panel where participants rank throat hit, is Marlboro® Filter Cigarettes, Gold Pack 100's, available from Phillips IGA.

As used herein, the term "chemosensory irritant" takes on its ordinary meaning in physiology and neuroscience, namely a substance capable of exhibiting a sensory irritation in an individual exposed to the substance. The irritation caused by a chemosensory irritant upon inhalation may be sensed, depending on the individual and the irritant, in the nose, mouth, throat, esophagus and/or lungs. The sensory effect in the throat is referred to in the definitions herein as "throat hit." Chemosensory irritation is most studied in the context of environmental and occupation health and safety, involving such things as air pollutants and indoor environmental irritants such as formaldehyde. See, for example, "Inhalation Toxicology," 2$^{nd}$ Edition, H. Salem et al., editors, Taylor & Francis Group (CRC), 2006. Besides subjective measurement of chemosensory irritation, such as panelists answering symptom questionnaires, various experimental techniques can be used to study chemical-induced irritation, such as examinations of functional changes, e.g. alterations in breathing frequency and pattern, nasal, bronchial and pulmonary function parameters, nasal mucosal swelling, acoustic rhinometry, eye-blinking frequency, tear film stability and chemosensory evoked potentials, in both humans and laboratory animals (see, S. K. Kjaergaar, et al., "The Assessment of Irritation Using Clinical Methods and Questionnaires," *American Industrial Hygiene Association,* 62(6):711-6, November 2001).

A chemosensory irritant for use in vaporizable alkaloid compositions of the present disclosure include those compounds capable of causing a physiological irritation of any one of the nose, mouth, throat, esophagus and lungs of an individual, wherein the physiological irritation is quantifiable. Examples of quantitative methods include, but are not limited to, measuring swelling of the nasal mucosa, peak airflows through the nose, acoustic rhinometry, and rhinostereometry for measuring thickness of the anterior nasal turbinate. Questionnaires are also useful for defining a set of symptoms to characterize dose-response relationships from controlled exposure studies.

In various embodiments, a chemosensory irritant for use in vaporizable alkaloid compositions herein is a substance capable of activating the chemosensory ion channels known as Transient Receptor Potential Channels, or TRP channels, as explained, for example, by H.J. Son, et al., "Activation of the Chemosensory Ion Channels TRPA1 and TRPV1 by Hydroalcohol Extract of *Kalopanax pictus* Leaves," *Biomol. Ther*. (Seoul), 2012 November; 20(6): 550-555. Besides the subset of chemosensory irritants defined herein below as "spice additives," many seemingly unrelated compounds are receptor agonists and are capable of activating one or more TRP channels (such as, A1, V1, V2, V3, V4, V5 or V6, M1, M2, M3, M4, M5, M6, M7, or M8 ion channels, and so forth), such as, for example, oleocanthal, 4-hydroxy-2-nonenal, 4-oxo-2-nonenal, allicin, allyl isothiocyanate, gingerol (included in the spice subset of irritants), icilin, polygodial, cinnamaldehyde, trans-p-methoxycinnamaldehyde, various cannabinoids, methyl syringate, 2-chlorobenzylidene malononitrile, 1-chloroacetophenone, ethyl bromoacetate, 4-hydroxyhexenal, toluene diisocyanate, p-benzoquinone, methyl p-hydroxybenzoate, flufenamic acid, niflumic acid, mefenamic acid, diclofenac, hydroxy-α-sanshool, 6-shogaol (included in the spice subset of irritants), 6-paradol, linalool, carvacrol, eugenol, thymol, vanillin, methyl eugenol, 2,6-dimethylphenol, 2,5-dimethylphenol, 3,4-dimethylphenol, 2,6-diisopropylphenol, caffeine, farnesyl thiosalicylic acid, 4-allylanisole, curcumin, capsicin (included in the spice subset of irritants), niacin, camphor, olvanil, and arvanil. Although nicotine is a known activator of TRPA1, it is excluded from consideration herein as a chemosensory irritant for vaporizable alkaloid compositions. See, for example, K. Talavera, et al., "Nicotine activates the chemosensory cation channel TRPA1," *Nature Neuroscience,* 12, 1293-1299 (2009). One aspect of the present disclosure is to provide vaporizable alkaloid compositions that are expressly devoid of nicotine such that they can be used as an alternative to smoking. An inventive aspect to the present compositions is that the compositions include a chemosensory irritant in place of nicotine so as to mimic the irritant effects of tobacco smoke.

Chemosensory irritants that find particular use in the present vaporizable alkaloid compositions include cannabinoids. In fact, certain TRP receptors are referred to as cannabinoid receptors, such CB1 and CB2. Six ion channels, TRPV1, TRPV2, TRPV3, TRPV4, TRPA1 and TRPM8 are known as ionotropic cannabinoid receptors, and thus those cannabinoids capable of binding to these receptors and activating ion channels are deemed chemosensory irritants for use in the vaporizable alkaloid compositions described herein. For a review of cannabinoids and TRP ion channel activation, see C. Muller, et al., "Cannabinoid Ligands Targeting TRP Channels," *Front. Mol. Neurosci.,* 11, 487 (2019).

Cannabinoids (endo-, phyto- and synthetic) capable of activating a TRP ion channel, and thus usable in the vaporizable alkaloid compositions of the present disclosure as chemosensory irritants include, but are not limited to, anandamide (AEA), 2-AG, NADA, OLDA, PEA, NGABA, NGly, NAsp, NSer, $\Delta^9$-tetrahydrocannabinol ($\Delta^9$-THC), $\Delta^9$-THCA, $\Delta^9$-THCV, $\Delta^9$-THCVA, CBD, CBDA, CBDV, CBG, CBGA, CBGV, CBN, CBC, and the synthetic cannabinoids WIN55,212-2, AM630, (R)-AM1241, (S)-AM1241, SR141716A, Gp-1a, AM251, SR144528, JWH133, HU308, HU910, CP55,940, and Nabilone. Of particular importance herein is CBD (cannabidiol), which has been found to be the most potent and efficacious phytocannabinoid agonist of TRPV1. Also, $\Delta^9$-THC has been identified as the most potent phytocannabinoid for activating TRPV2, although $\Delta^9$-THC is not selective seeing that it also activates TRPA1.

Further, chemosensory irritants that activate a TRP ion channel, and thus find use in the vaporizable alkaloid compositions herein, include numerous compounds naturally occurring in various plants, trees, shrubs, roots, flowers, fruits, seeds and nuts. Such compounds are disclosed, for example, by J. Vriens, et al., "Herbal Compounds and Toxins Modulating TRP Channels," *Curr. Neuropharmacol.,* 2008 March; 6(1): 79-96. In various embodiments, in addition to the "spice additives" defined and discussed herein that include such compounds as capsaicinoids, gingerols and shogaols, other TRP channel activators are of use herein and include, but are not limited to, resiniferanoids from *Euphorbia reinifera*, eugenol from *Euenia carophyllata* and *Ocimum gratissiumum*, ginsenosides from *Panax*, zingerone and paradol derived from heating or dehydrating gingerol or from *Aframomum melgueta* seeds, *Evodia* compounds from *Evodia rutaecarpa*, various unsaturated 1,4-dialdehyde sesquiterpenes isolated from *Drymis winteri*, such as polygodial, isovelleral and drimanial, other 1,4-dialdehyde terpenes from *Cinnamosma fragrans*, such as cinnamodial, cinnamosmolide, and cinnamolide, or warbuganal from *Warburgia* plants. In vitro assays used to measure activation of TRP ion channels are found, for example, in R. Lehmann, et al., "Alternative in vitro assays to assess the potency of sensory irritant—Is one TRP channel enough?", *Neurotoxicology,* 2017 May; 60:178-186, and J. M. Martinez, et al., Activation of TRPA1 by volatile organic chemicals leading to sensory irritation," ALTEX 2019; 36(4): 572-582. Of further importance for use herein are the phytochemicals present in *Scutellaria baicalensis* (most particularly the phytochemicals baicalein, baicalin, wogonin, norwogonin, oroxylin A and β-sitosterol), *Vitex agnus, Pterodon pubescens, Croton macrostachyus, Angelicae pubescentis, Ephedra sinica, Amphilophium crucigerum, Bosewellia carterii, Commiphora myrrha, Echinophora platyloba, Nypa fruti-* cans, *Zingiber officiale* (presented under the spice additives subset of irritants), *Corydalis saxicola, Coptis chinensis, Ononis spinosa, Parkia platycephala, Piper nigrum* (presented under the spice additives subset of irritants), and *Cymbopogon citratus*. Chemosensory irritants for use herein can be first assessed by in vitro non-animal sensory irritation assays, followed by consumer sensory panels to evaluate subtle physiological effects and to determine dose levels and user acceptance.

As used herein, the term "spice additive" refers to an organic substance capable of producing a throat hit or other similar "hot," "irritative," or otherwise "burning" sensation at least at the back of the throat, and optionally in the mouth and on the lips, when the spice additive is in a vaporizable alkaloid composition that is vaporized and inhaled by an individual, such as a person vaping. Spice additives herein form a subset of chemosensory irritants and are known to activate one or more of the TRP ion channels. Since a group of these compounds might at first seem structurally unrelated, a "spice additive" herein can be clearly defined as an organic substance having a spiciness or "heat" in the range of from about 1,000 to about 20,000,000 Scoville Heat Units (SHU). At the lower end of the Scoville scale, compounds for use herein include, but are not limited to, gingerol (60,000 SHU), piperine (100,000 SHU) and Shogaol (160,000 SHU). In more preferred embodiments, a spice additive for use in the vaporizable alkaloid compositions herein will have a Scoville rating of from about 100,000 to about 20,000,000 SHU, and more preferably from about 10,000,000 to about 20,000,000 SHU and will include all of the known capsaicinoids such as capsaicin (16,000,000 SHU) and dihydrocapsaicin (15,000,000 SHU), along with uncharacterized capsaicinoids that are likely isomers of the known ones. Although chemically unrelated to capsaicinoids, compounds such as piperine (100,000 SHU) and Shogaol (160,000 SHU) find use in the present compositions. A capsaicinoid spice additive for use herein includes, but is not limited to, capsaicin, dihydrocapsaicin, norcapsaicin, nordihydrocapsaicin, homocapsaicin, homodihydrocapsaicin, and mixtures thereof. An isolated capsaicinoid chemically pure or otherwise is not necessary for the vaporizable alkaloid compositions herein, as it is also convenient to prepare the various compositions with an extract of a spice additive. For example, capsaicinoids can be extracted from chili peppers or other peppers using room temperature or boiling ethanol (such as in a Soxhlet extractor). The resulting red ethanol solution can then be used as is (referred to as a "capsaicin liquid" or "liquid capsaicin") or evaporated to leave behind a thick, dark red viscous mixture of capsaicinoids (the red color believed to be from β-carotene). See, for example, F. Martins, et al., "Novel Approaches to Extraction Methods in Recovery of Capsaicin from Habanero Pepper (CNPH 15.192)," *Pharmacogn. Mag.* 2017 July; 13(Suppl 2): S375-S379, and Y. Zhu, "Multi-Dimensional Pungency and Sensory Profiles of Powder and Oil of Seven Chili Peppers Based On Descriptive Analysis and Scoville Heat Units," *Food Chemistry*, 411, 15 Jun. 2023, Article 135488.

As used herein, the term "liquid capsaicin" or "capsaicin liquid" refers to an ethanolic or other solvent extract of a fruit obtained from a plant of the genus *Capsicum annuum*, such as various chili peppers. A liquid capsaicin preferred for use herein comprises about 0.9 wt. % capsaicinoids in ethanol and is available from Olive Nation, LLC, Avon, MA under the name *Capsicum* Flavor Extract.

It should be noted that "flavoring agents," optional to the vaporizable alkaloid compositions herein, are defined separately from and are entirely distinguished from "chemosensory irritants and the subset of irritants referred to herein as "spice additives."

As used herein, a "flavoring agent" takes on its ordinary meaning in food science, with the caveat that a flavoring agent herein purposely excludes compounds containing a capsaicinoid, meaning that flavoring agents herein by definition have no measurable or calculable Scoville heat rating and thus are distinct from spice additive defined herein above. Flavoring agents for use herein include, but are not limited to, ethyl maltol, ethyl butyrate, ethyl acetate, maltol, ethyl vanillin, furaneol, methyl cyclopenenolone, δ-decalactone, γ-decalactone, cis-3-hexanol, iso-amyl acetate, ethyl-2-methyl butyrate, butyric acid, linalool, benzyl alcohol, ethyl hexanoate, benzaldehyde, iso-amyl isovalerate, hexanoic acid, ethyl propionate, γ-undecalactone, and hexyl acetate.

As used herein, the term "about" refers to a quantity, level, value, number, frequency, percentage, dimension, size, amount, weight or length that varies by as much as 10, 9, 8, 7, 6, 5, 4, 3, 2 or 1% to a reference quantity, level, value, number, frequency, percentage, dimension, size, amount, weight or length. For example, a quantity expressed as being "about 5 wt. %" includes a variance of up to 4.5 to 5.5 wt. %.

As used herein, the term "smoking cessation program" refers to a plan provided by a medical clinic, a dispensary, or any other business enterprise to a current smoker to help that individual stop smoking. In various embodiments, a smoking cessation program herein includes providing the individual in need thereof vaping liquids (or providing disposable electronic devices preloaded with vaping liquids) designed to help the individual follow the prescribed program and reduce and/or ultimately eliminate smoking. In certain examples, the clinic, dispensary or other business enterprise will meet with the individual placed on the cessation program on a recurring basis to interview the individual as to compliance and to supply that individual with customized vaporizable compositions designed to gradually move the smoker entirely over to electronic vaping.

General Embodiments

Vaporizable alkaloid compositions in accordance with the present disclosure are optimized to provide an improved user experience. The experience an individual experiences from inhaling a vaporized liquid delivered from an electronic device can be, and arguably should be, similar if not identical to the experience a user would have from smoking a burning cigarette, but this can only be achieved if certain interrelated sensory effects are balanced, including throat hit, head rush, nasal and oral sensations and taste, and cloud appearance. These factors make up the user experience.

It has now been surprising discovered that an improved user experience relies on having a unique combination and critical amounts and ratios of a substituted pyridine compound, or salt or mixed salt thereof, and a spice additive capable of providing more of a perceived throat hit than would otherwise be obtained from inhaling propylene glycol vapor alone. The vaporizable and inhalable compositions of the present disclosure rely on precise amounts of substituted pyridine compound, or salt or mixed salt thereof, and spice additive, and their ratios. Further, having at some corresponding organic acid salt of the substituted pyridine compound in the inhalable compositions mitigates harshness and ensures the user experiences a desired head rush but with a perceivable smoothness.

In various embodiments, a vaporizable alkaloid composition herein comprises:
at least one substituted pyridine compound of Formula (I), or salt or mixed salt thereof;

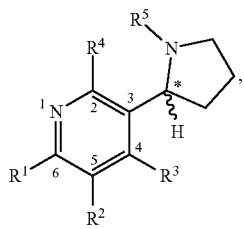

(I)

wherein $R^1$, $R^2$, $R^3$, $R^4$, and $R^5$ are independently selected from H, alkyl, substituted alkyl, cycloalkyl, substituted cycloalkyl, alkenyl, and substituted alkenyl, with the proviso that if $R^5$ is $CH_3$, then $R^1$, $R^2$, $R^3$, and $R^4$ cannot all be H;
at least one chemosensory irritant;
at least one solvent; and,
optionally, at least one flavoring agent,
wherein the vaporizable alkaloid composition is entirely devoid of nicotine.

In various embodiments, the at least one chemosensory irritant is a phytochemical, such as a compound found in or an extract of *Scutellaria baicalensis, Cannabis sativa* or *Cannabis indica*, such as baicalein, baicalin, wogonin, nor-wogonin, oroxylin A, β-sitosterol, cannabidiol, anandamide and $\Delta^9$-tetrahydrocannabinol.

In various embodiments, the at least one chemosensory irritant is a spice additive having a spiciness of from about 1,000 to about 20,000,000 Scoville Heat Units (SHU), such as capsaicin, shogaol and gingerol.

Alternatives for each of these components in the compositions are described below and above in the definitions section.

1. Alkaloid Compounds and Salts or Mixed Salts Thereof

In various embodiments, a vaporizable alkaloid composition herein comprises at least one substituted pyridine compound, or salt, or mixed salt thereof, according to Formula (I):

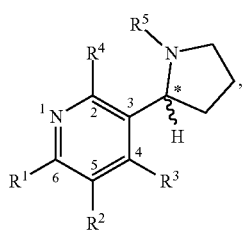

(I)

wherein $R^1$, $R^2$, $R^3$, $R^4$, and $R^5$ are independently selected from H, alkyl, substituted alkyl, cycloalkyl, substituted cycloalkyl, alkenyl, and substituted alkenyl, with the proviso that if $R^5$ is $CH_3$, then $R^1$, $R^2$, $R^3$, and $R^4$ cannot all be H. This proviso language expressly excludes both (R) and (S) enantiomers of nicotine from consideration in the compositions according to the present disclosure.

Vaporizable alkaloid compositions of the present disclosure are designed for use in smoking cessation programs and are preferably absent nicotine. As such, a chemosensory irritant for use in a vaporizable alkaloid composition herein expressly excludes both (R) and (S) enantiomers of nicotine from consideration even though nicotine is a known chemosensory irritant.

In various embodiments, a vaporizable alkaloid composition in accordance with the present disclosure comprises from about 1 wt. % to about 80 wt. % of a substituted pyridine compound of Formula (I) as added to the composition. In more preferred embodiments, a vaporizable alkaloid composition in accordance with the present disclosure comprises from about 4 wt. % to about 20 wt. % of a substituted pyridine compound as added to the composition, such as to target the w/v amount of substituted pyridine compound at about 100 to about 250 mg/mL. In more preferred embodiments, a vaporizable alkaloid composition in accordance with the present disclosure comprises from about 4 wt. % to about 12 wt. % of a substituted pyridine compound as added to the composition, such as to target the w/v amount of substituted pyridine compound at about 100 mg/mL.

"As added" refers to what is added to a batch, regardless of whether any reactions take place between components in the composition, such as reaction of free base alkaloid with organic acid to form at least some alkaloid salt.

It should be noted in Formula (I) that the carbon center of the pyrrolidine ring marked (*) is always a chiral center regardless of the choices for $R^1$, $R^2$, $R^3$, $R^4$ and $R^5$.

In various examples, a substituted pyridine compound in accordance with Formula (I) is a racemic mixture of (R) and (S) at the indicated chiral center (*), such as obtained by a nonchiral synthesis.

In various examples, a substituted pyridine compound in accordance with Formula (I) is only the (S) enantiomer at the indicated chiral center (*), such as obtained by a chiral synthesis or by separation of enantiomers from a racemic mixture. In certain examples, the (S)-substituted pyridine compound of Formula (I) is the preferred alkaloid for vaporizable alkaloid compositions herein.

In various examples, a substituted pyridine compound in accordance with Formula (I) is only the (R) enantiomer at the indicated chiral center (*), such as obtained by a chiral synthesis or by separation of enantiomers. In certain examples, the (R)-substituted pyridine compound of Formula (I) is the unfavorable alkaloid for vaporizable alkaloid compositions herein because of its potentially adverse physiological effects when inhaled.

In various embodiments, and independent of $R^5$, at least one of $R^1$, $R^2$, $R^3$, and $R^4$ is methyl, and the remaining $R^1$, $R^2$, $R^3$, and $R^4$ substituents that are not methyl are H.

In various embodiments, $R^5$ is $CH_3$ and at least one of $R^1$, $R^2$, $R^3$, and $R^4$ is not H.

In various embodiments, $R^1$, $R^2$, $R^3$, $R^4$ and $R^5$ are each H.

In various embodiments, $R^5$ is —$(CH_2)$n-$NR^6R^7$, wherein n is an integer from 1 to 10, and wherein $R^6$ and $R^7$ are independently selected from H, alkyl, substituted alkyl, cycloalkyl, substituted cycloalkyl, alkenyl and substituted alkenyl, or $R^6$ and $R^7$ together with the N atom to which they are bonded form a 3-8 membered optionally substituted heterocyclic ring, including for example, aziridine, azetidine, pyrrolidine, piperidine, 1,4-piperazine, and morpholine. In various embodiments, and independent of $R^1$, $R^2$, $R^3$, and $R^4$, $R^5$ is selected from —$(CH_2)$—$NH_2$; —$(CH_2)_2$—$NH_2$; —$(CH_2)_3$—$NH_2$; —$(CH_2)_4$—$NH_2$;

—(CH$_2$)$_5$—NH$_2$; —(CH$_2$)$_6$—NH$_2$; —(CH$_2$)$_7$—NH$_2$; —(CH$_2$)$_8$—NH$_2$; —(CH$_2$)$_9$—NH$_2$; —(CH$_2$)$_{10}$—NH$_2$; —(CH$_2$)—N(CH$_3$)$_2$; —(CH$_2$)$_2$—N(CH$_3$)$_2$; —(CH$_2$)$_3$—N(CH$_3$)$_2$; —(CH$_2$)$_4$—N(CH$_3$)$_2$; —(CH$_2$)$_5$—N(CH$_3$)$_2$; —(CH$_2$)$_6$—N(CH$_3$)$_2$; —(CH$_2$)$_7$—N(CH$_3$)$_2$; —(CH$_2$)$_8$—N(CH$_3$)$_2$; —(CH$_2$)$_9$—N(CH$_3$)$_2$; and —(CH$_2$)$_{10}$—N(CH$_3$)$_2$.

In various embodiments, and independent of R$^1$, R$^2$, R$^3$, and R$^4$, R$^5$ is selected from:

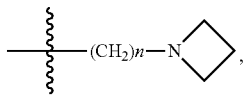

wherein n is 1-10;

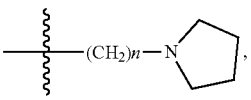

wherein n is 1-10;

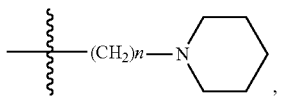

wherein n is 1-10;

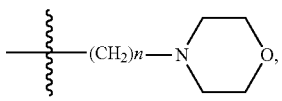

wherein n is 1-10; and

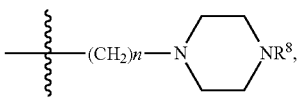

wherein n is 1-10; and R$^8$ is selected from H, alkyl, substituted alkyl, cycloalkyl, substituted cycloalkyl, alkenyl, and substituted alkenyl.

In various embodiments, and independent of R$^1$, R$^2$, R$^3$, and R$^4$, R$^5$ is:

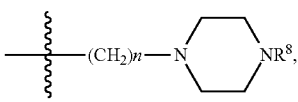

wherein n is 1-10; and R$^8$ is H or CH$_3$.

In various embodiments, R$^5$ is H, and at least one of R$^1$, R$^2$, R$^3$, and R$^4$ is —(CH$_2$)n-NR$^6$R$^7$, wherein n is an integer from 1 to 10, and wherein R$^6$ and R$^7$ are independently selected from H, alkyl, substituted alkyl, cycloalkyl, substituted cycloalkyl, alkenyl and substituted alkenyl, or R$^6$ and R$^7$ together with the N atom to which they are bonded form a 3-8 membered optionally substituted heterocyclic ring.

In various embodiments, R$^5$ is CH$_3$, and at least one of R$^1$, R$^2$, R$^3$, and R$^4$ is —(CH$_2$)n-NR$^6$R$^7$, wherein n is an integer from 1 to 10, and wherein R$^6$ and R$^7$ are independently selected from H, alkyl, substituted alkyl, cycloalkyl, substituted cycloalkyl, alkenyl and substituted alkenyl, or R$^6$ and R$^7$ together with the N atom to which they are bonded form a 3-8 membered optionally substituted heterocyclic ring.

In various embodiments, R$^5$ is CH$_3$, and at least one of R$^1$, R$^2$, R$^3$, and R$^4$ is —(CH$_2$)n-N(CH$_3$)$_2$, wherein n is an integer from 1 to 10.

In various embodiments, substituted pyridine compounds of Formula (I) for use in vaporizable alkaloid compositions herein include, but are not limited to, (R) or (S)-3-(pyrrolidin-2-yl)pyridine, (R) or (S)-2-methyl-3-(1-methylpyrrolidin-2-yl)pyridine, (R) or (S)-4-methyl-3-(1-methylpyrrolidin-2-yl)pyridine, (R) or (S)-3-methyl-5-(1-methylpyrrolidin-2-yl)pyridine, (R) or (S)-2-methyl-5-(1-methylpyrrolidin-2-yl)pyridine, (R) or (S)-2,6-dimethyl-3-(1-methylpyrrolidin-2-yl)pyridine, (R) or (S)-2,4-dimethyl-5-(1-methylpyrrolidin-2-yl)pyridine, (R) or (S)-2,3-dimethyl-5-(1-methylpyrrolidin-2-yl)pyridine, (R) or (S)-2,4-dimethyl-3-(1-methylpyrrolidin-2-yl)pyridine, (R) or (S)-2,5-dimethyl-3-(1-methylpyrrolidin-2-yl)pyridine, (R) or (S)-3,4-dimethyl-5-(1-methylpyrrolidin-2-yl)pyridine, (R) or (S)-1-(2-aminoethyl)-2-(3-pyridyl)pyrrolidine, (R) or (S)-1-(3-aminopropyl)-2-(3-pyridyl)pyrrolidine, (R) or (S)-1-(4-aminobutyl)-2-(3-pyridyl)pyrrolidine, (R) or (S)-1-(5-aminopentyl)-2-(3-pyridyl)pyrrolidine, (R) or (S)-1-(2-dimethylaminoethyl)-2-(3-pyridyl)pyrrolidine, (R) or (S)-1-(3-dimethylaminopropyl)-2-(3-pyridyl)pyrrolidine, (R) or (S)-1-(4-dimethylaminobutyl)-2-(3-pyridyl)pyrrolidine, (R) or (S)-3-(2-(6-methylpyridin-3-yl)pyrrolidin-1-yl)propanenitrile, (R) or (S)-4-(2-(6-methylpyridin-3-yl)pyrrolidin-1-yl)butanenitrile, (R) or (S)-1-(3-aminopropyl)-2-(6-methyl-3-pyridyl)pyrrolidine, (R) or (S)-1-[3-(N,N-dimethylamino)propyl]-2-(6-methyl-3-pyridyl)pyrrolidine, (R) or (S)-1-(N,N-diethyl-3-aminopropyl-2-(3-pyridyl)pyrrolidine, (R) or (S)-3-(1-(2-(pyrrolidin-1-yl)ethyl)pyrrolidin-2-yl)pyridine, (R) or (S)-3-(1-(2-(piperidin-1-yl)ethyl)pyrrolidin-2-yl)pyridine, (R) or (S)-4-(2-(2-(pyridin-3-yl)pyrrolidin-1-yl)ethyl)morpholine, (R) or (S)-3-(1-(3-(pyrrolidin-1-yl)propyl)pyrrolidin-2-yl)pyridine, (R) or (S)-3-(1-(3-(piperidin-1-yl)propyl)pyrrolidin-2-yl)pyridine, and (R) or (S)-4-(3-(2-(pyridin-3-yl)pyrrolidin-1-yl)propyl)morpholine.

In various embodiments, substituted pyridine compounds of Formula (I) for use in vaporizable alkaloid compositions herein also include, but are not limited to:

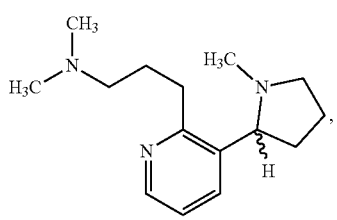

(2)

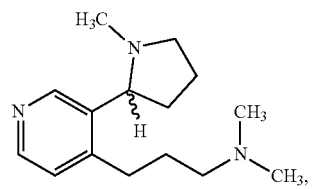

(3)

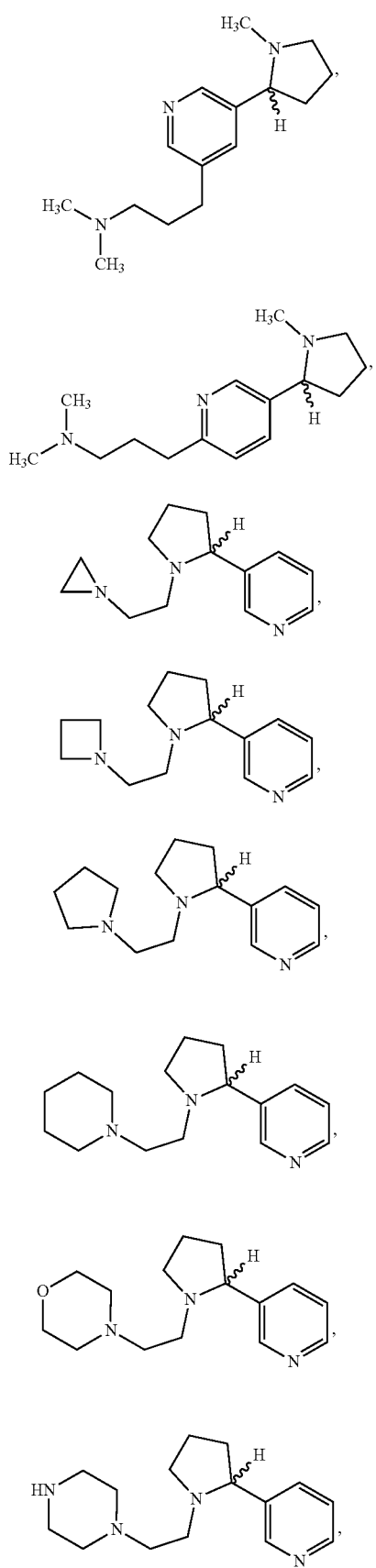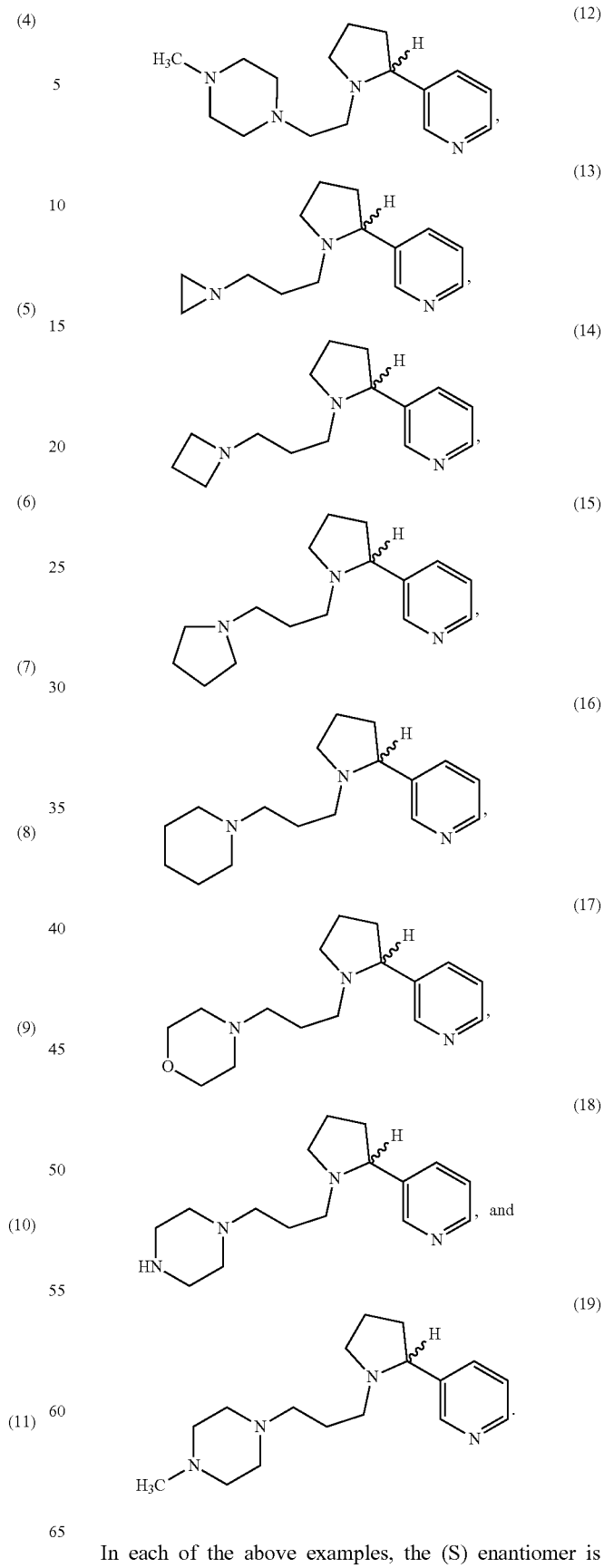
In each of the above examples, the (S) enantiomer is likely active as a nicotinic acetylcholine receptor ligand and is preferred, whereas the (R) enantiomer is likely physiologically inert or possibly even metabolically toxic. Thus, in preferred embodiments, the racemic mixture is not used for any of these alkaloids.

In various embodiments, $R^1$, $R^2$, $R^3$, $R^4$ and $R^5$ are independently selected from H, methyl, ethyl, n-propyl, iso-propyl, tert-butyl, cyclopropyl, cyclobutyl, cyclopentyl and cyclohexyl, with the proviso that if $R^5$ is methyl, then $R^1$, $R^2$, $R^3$, and $R^4$ cannot all be H.

In preferred examples, $R^1$ and $R^5$ are both methyl, $R^2$, $R^3$, and $R^4$ are each H, and the chiral center (*) is in the (S)-configuration.

Of particular interest for the present compositions is (S)-2-methyl-5-(1-methylpyrrolidin-2-yl)pyridine, a compound having the chemical structure (1):

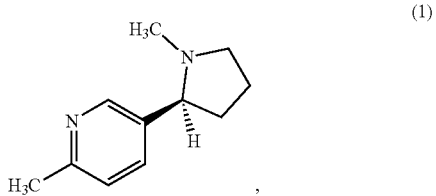

(1)

or salts thereof, or mixed salts thereof.

A chiral synthesis of alkaloid (1) was disclosed by C. G. Chavdarian, et al. in U.S. Pat. No. 4,321,387 issued to Philip Morris, Inc. in 1982. This compound can be made by the synthesis route of Philip Morris, or by another suitable chiral synthesis route known or devised by one of skill in the art, or obtained by a commercial supplier such as, for example, Toronto Research Chemicals, Toronto, Ontario, Canada having catalog number M323270.

Salts or mixed salts of an alkaloid of Formula (I) are of use herein and are obtainable by straightforward reaction of a substituted pyridine compound (I) with an inorganic or preferably an organic acid $R^9$—$CO_2H$ or mixture of organic acids, in a suitable solvent, at ambient reaction conditions or with heating. $R^9$ is selected accordingly for the corresponding organic acid desired (e.g., $R^9$=H for formic acid, $R^9$=$CH_3$ for acetic acid, $R^9$=—$CH(CO_2H)$—$CH_2$—$CO_2H$ for citric acid, and so forth), so $R^9$ is selected from alkyl, cycloalkyl, aryl, and heterocyclyl, any of which may be optionally substituted.

Reaction Scheme A sets forth this general synthesis of alkaloid salts for use in the vaporizable alkaloid compositions of the present disclosure when using an organic rather than inorganic acid:

Reaction Scheme A—General Synthesis of Alkaloid Salts

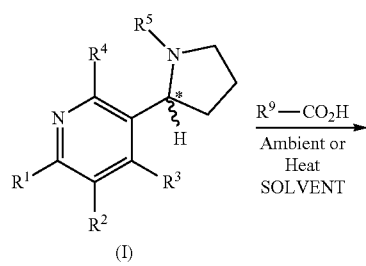

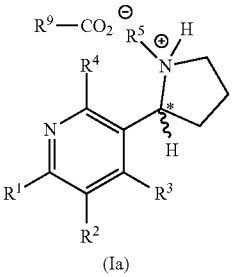

(Ia)

In the above Reaction Scheme A, and although one might precisely know the molar ratio of free base alkaloid (I) to acid $R^9$—$CO_2H$ or mixture of acids in a composition, no attempt is made to quantify or characterize the resulting salts or mixed salts (Ia) or to quantify the reaction completeness, recognizing that some organic acids are more than monohydric and may also act as chelating agents. Various acid to base ratios may be formed (i.e., something other than 1:1 acid to base salts). For example, nicotine salts, made from a variety of organic acids, have been described by T. A. Perfetti, "Structural Study of Nicotine Salts," *Beiträge zur Tabakforschung International*, 12(2), 43-54, 1983, wherein 1:1, 2:1 and 3:1 acid to base ratios were seen with nicotine. In this reference, Perfetti discloses that nicotine forms a 3:1 acid to base salts with aliphatic monocarboxylic acids, such as acetic acid, wherein one acid molecule is bound as in the 1:1 salts and the other two acid molecules are bound to the nitrogen of the pyridine ring, and that benzoate salts are 1:1 acid to base salts. Perfetti discloses that the citrate salt of nicotine is a 2:1 acid to base salt. So, if $R^9$—$CO_2H$ represents a mixture of organic acids, the resulting alkaloid salts (Ia) might not be characterizable.

In Reaction Scheme A above, the organic acid $R^9$—$CO_2H$ can be any of the acids disclosed herein, including formic acid, acetic acid, trifluoroacetic acid, aspartic acid, butanoic acid, butyric acid, 2-methylbutyric acid, 3-methylbutyric acid, benzoic acid, caprylic acid, citric acid, crotonic acid, ethylenediaminetetraacetic acid, fumaric acid, gluconic acid, glutamic acid, glyceric acid, glycolic acid, lactic acid, lauric acid, levulinic acid, maleic acid, malic acid, malonic acid, mandelic acid, methane sulfonic acid, oxalic acid, phenylacetic acid, phthalic acid, picric acid, propionic acid, pyruvic acid, salicylic acid, stearic acid, succinic acid, tannic acid, tartaric acid, tartronic acid, valeric acid, and mixtures thereof. Preferred for use herein is citric acid, acetic acid, benzoic acid, tartaric acid, lactic acid, salicylic acid, malic acid, levulinic acid, and mixtures thereof.

In Reaction Scheme A above, the solvent may be chosen on the basis of it being appropriate, i.e., pharmaceutically acceptable or otherwise deemed "safe," for a composition intended to be vaporized and inhaled. In other words, recognizing that this acid/base reaction can be performed in situ, the alkaloid salts (Ia) would not be isolated, but rather the resulting reaction mixture becomes the vaporizable alkaloid composition in accordance with the present disclosure. In these instances, the solvents are selected from the group consisting of propylene glycol, glycerin, ethanol, water, and mixtures thereof. Typically, Reaction Scheme A can be conducted in a solvent mixture of propylene glycol/ethanol with small amounts of water (such as entrained in the reaction from use of 190 proof ethanol). If necessary, the final reaction mixture can be cooled and filtered prior to use in an electronic device.

In preferred embodiments, a deficient amount of organic acid $R^9$—$CO_2H$ is used in Reaction Scheme A (or in the composition if conducted in situ) such that a mixture of alkaloid salt and unreacted alkaloid free base result and thus remain present together in the vaporizable alkaloid composition. In less preferred embodiments, a sufficient amount or an excess of organic acid $R^9$—$CO_2H$ is used in the reaction to drive salt formation to completion, such that there may likely be no free base alkaloid remaining at all.

In various embodiments, it is preferable to have a molar excess of substituted pyridine free base compound to the one or more organic acids such that the formation of alkaloid salts is an incomplete reaction and such that the vaporizable alkaloid composition comprises both alkaloid organic acid salt and unreacted alkaloid free base.

In various embodiments, given the typical amount of substituted pyridine compound to be from about 1 wt. % to about 80 wt. %, a vaporizable alkaloid composition herein comprises from about 0.05 wt. % to about 1.5 wt. %, preferably about 0.05 wt. % to about 0.15 wt. % total organic acid(s), based on the total weight of the composition.

In various embodiments, the molar ratio of substituted pyridine free base compound to total organic acid(s) $R^9$—$CO_2H$ is from about 25:1 to about 75:1, and more preferably about 50:1. This ratio can be held constant, such that in compositions where the amount of substituted pyridine free base compound is increased, the amount of total organic acid(s) $R^9$—$CO_2H$ may also be increased so as to maintain this molar ratio.

It should be emphasized that it is not necessary to isolate any of the desired salts of substituted pyridine compounds for use in the vaporizable alkaloid compositions. A vaporizable alkaloid composition can be prepared by combining a substituted pyridine free base compound with the desired organic acid(s) in a solvent system, wherein the alkaloid salts are formed in situ and the reaction mixture thus formed is the vaporizable alkaloid composition.

In various preferred embodiments, (S)-2-methyl-5-(1-methylpyrrolidin-2-yl)pyridine is reacted with an organic acid selected from the group consisting of acetic acid, benzoic acid, citric acid, lactic acid, levulinic acid, malic acid, salicylic acid, tartaric acid, and mixtures thereof. In more preferred embodiments, (S)-2-methyl-5-(1-methylpyrrolidin-2-yl)pyridine is reacted with a molar deficiency of a combination of citric acid and acetic acid.

For vaporizable alkaloid compositions of the present disclosure, preferred salts and mixed salts of substituted pyridine compounds of Formula (I) include, but are not limited to:

(2S)-1-methyl-2-(6-methylpyridin-3-yl)pyrrolidin-1-ium acetate,
(2S)-1-methyl-2-(5-methylpyridin-3-yl)pyrrolidin-1-ium acetate,
(2S)-1-methyl-2-(4-methylpyridin-3-yl)pyrrolidin-1-ium acetate,
(2S)-1-methyl-2-(2-methylpyridin-3-yl)pyrrolidin-1-ium acetate,
(2S)-2-(2,4-dimethylpyridin-3-yl)-1-methylpyrrolidin-1-ium acetate,
(2S)-2-(2,5-dimethylpyridin-3-yl)-1-methylpyrrolidin-1-ium acetate,
(2S)-2-(2,6-dimethylpyridin-3-yl)-1-methylpyrrolidin-1-ium acetate,
(2S)-2-(4,5-dimethylpyridin-3-yl)-1-methylpyrrolidin-1-ium acetate,
(2S)-2-(4,6-dimethylpyridin-3-yl)-1-methylpyrrolidin-1-ium acetate,
(2S)-2-(5,6-dimethylpyridin-3-yl)-1-methylpyrrolidin-1-ium acetate,
(2S)-1-methyl-2-(6-methylpyridin-3-yl)pyrrolidin-1-ium citrate,
(2S)-1-methyl-2-(5-methylpyridin-3-yl)pyrrolidin-1-ium citrate,
(2S)-1-methyl-2-(4-methylpyridin-3-yl)pyrrolidin-1-ium citrate,
(2S)-1-methyl-2-(2-methylpyridin-3-yl)pyrrolidin-1-ium citrate,
(2S)-2-(2,4-dimethylpyridin-3-yl)-1-methylpyrrolidin-1-ium citrate,
(2S)-2-(2,5-dimethylpyridin-3-yl)-1-methylpyrrolidin-1-ium citrate,
(2S)-2-(2,6-dimethylpyridin-3-yl)-1-methylpyrrolidin-1-ium citrate,
(2S)-2-(4,5-dimethylpyridin-3-yl)-1-methylpyrrolidin-1-ium citrate,
(2S)-2-(4,6-dimethylpyridin-3-yl)-1-methylpyrrolidin-1-ium citrate,
(2S)-2-(5,6-dimethylpyridin-3-yl)-1-methylpyrrolidin-1-ium citrate,
(2S)-1-methyl-2-(6-methylpyridin-3-yl)pyrrolidin-1-ium citrate/acetate,
(2S)-1-methyl-2-(5-methylpyridin-3-yl)pyrrolidin-1-ium citrate/acetate,
(2S)-1-methyl-2-(4-methylpyridin-3-yl)pyrrolidin-1-ium citrate/acetate,
(2S)-1-methyl-2-(2-methylpyridin-3-yl)pyrrolidin-1-ium citrate/acetate,
(2S)-2-(2,4-dimethylpyridin-3-yl)-1-methylpyrrolidin-1-ium citrate/acetate,
(2S)-2-(2,5-dimethylpyridin-3-yl)-1-methylpyrrolidin-1-ium citrate/acetate,
(2S)-2-(2,6-dimethylpyridin-3-yl)-1-methylpyrrolidin-1-ium citrate/acetate,
(2S)-2-(4,5-dimethylpyridin-3-yl)-1-methylpyrrolidin-1-ium citrate/acetate,
(2S)-2-(4,6-dimethylpyridin-3-yl)-1-methylpyrrolidin-1-ium citrate/acetate,
(2S)-2-(5,6-dimethylpyridin-3-yl)-1-methylpyrrolidin-1-ium citrate/acetate,
(2S)-1-methyl-2-(6-methylpyridin-3-yl)pyrrolidin-1-ium benzoate,
(2S)-1-methyl-2-(5-methylpyridin-3-yl)pyrrolidin-1-ium benzoate,
(2S)-1-methyl-2-(4-methylpyridin-3-yl)pyrrolidin-1-ium benzoate,
(2S)-1-methyl-2-(2-methylpyridin-3-yl)pyrrolidin-1-ium benzoate,
(2S)-2-(2,4-dimethylpyridin-3-yl)-1-methylpyrrolidin-1-ium benzoate,
(2S)-2-(2,5-dimethylpyridin-3-yl)-1-methylpyrrolidin-1-ium benzoate,
(2S)-2-(2,6-dimethylpyridin-3-yl)-1-methylpyrrolidin-1-ium benzoate,
(2S)-2-(4,5-dimethylpyridin-3-yl)-1-methylpyrrolidin-1-ium benzoate,
(2S)-2-(4,6-dimethylpyridin-3-yl)-1-methylpyrrolidin-1-ium benzoate,
(2S)-2-(5,6-dimethylpyridin-3-yl)-1-methylpyrrolidin-1-ium benzoate,
(2S)-1-methyl-2-(5-methylpyridin-3-yl)pyrrolidin-1-ium ditartrate,
(2S)-1-methyl-2-(4-methylpyridin-3-yl)pyrrolidin-1-ium ditartrate, (2S)-1-methyl-2-(2-methylpyridin-3-yl)pyrrolidin-1-ium ditartrate,
(2S)-2-(2,4-dimethylpyridin-3-yl)-1-methylpyrrolidin-1-ium ditartrate,
(2S)-2-(2,5-dimethylpyridin-3-yl)-1-methylpyrrolidin-1-ium ditartrate,
(2S)-2-(2,6-dimethylpyridin-3-yl)-1-methylpyrrolidin-1-ium ditartrate,
(2S)-2-(4,5-dimethylpyridin-3-yl)-1-methylpyrrolidin-1-ium ditartrate,
(2S)-2-(4,6-dimethylpyridin-3-yl)-1-methylpyrrolidin-1-ium ditartrate,
(2S)-2-(5,6-dimethylpyridin-3-yl)-1-methylpyrrolidin-1-ium ditartrate,
(2S)-1-methyl-2-(5-methylpyridin-3-yl)pyrrolidin-1-ium lactate,
(2S)-1-methyl-2-(4-methylpyridin-3-yl)pyrrolidin-1-ium lactate,
(2S)-1-methyl-2-(2-methylpyridin-3-yl)pyrrolidin-1-ium lactate,
(2S)-2-(2,4-dimethylpyridin-3-yl)-1-methylpyrrolidin-1-ium lactate,
(2S)-2-(2,5-dimethylpyridin-3-yl)-1-methylpyrrolidin-1-ium lactate,
(2S)-2-(2,6-dimethylpyridin-3-yl)-1-methylpyrrolidin-1-ium lactate,
(2S)-2-(4,5-dimethylpyridin-3-yl)-1-methylpyrrolidin-1-ium lactate,
(2S)-2-(4,6-dimethylpyridin-3-yl)-1-methylpyrrolidin-1-ium lactate,
(2S)-2-(5,6-dimethylpyridin-3-yl)-1-methylpyrrolidin-1-ium lactate,
(2S)-1-methyl-2-(5-methylpyridin-3-yl)pyrrolidin-1-ium levulinate,
(2S)-1-methyl-2-(4-methylpyridin-3-yl)pyrrolidin-1-ium levulinate,
(2S)-1-methyl-2-(2-methylpyridin-3-yl)pyrrolidin-1-ium levulinate,
(2S)-2-(2,4-dimethylpyridin-3-yl)-1-methylpyrrolidin-1-ium levulinate,
(2S)-2-(2,5-dimethylpyridin-3-yl)-1-methylpyrrolidin-1-ium levulinate,
(2S)-2-(2,6-dimethylpyridin-3-yl)-1-methylpyrrolidin-1-ium levulinate,
(2S)-2-(4,5-dimethylpyridin-3-yl)-1-methylpyrrolidin-1-ium levulinate,
(2S)-2-(4,6-dimethylpyridin-3-yl)-1-methylpyrrolidin-1-ium levulinate,
(2S)-2-(5,6-dimethylpyridin-3-yl)-1-methylpyrrolidin-1-ium levulinate,
(2S)-1-methyl-2-(4-methylpyridin-3-yl)pyrrolidin-1-ium malate,
(2S)-1-methyl-2-(2-methylpyridin-3-yl)pyrrolidin-1-ium malate,
(2S)-2-(2,4-dimethylpyridin-3-yl)-1-methylpyrrolidin-1-ium malate,
(2S)-2-(2,5-dimethylpyridin-3-yl)-1-methylpyrrolidin-1-ium malate,
(2S)-2-(2,6-dimethylpyridin-3-yl)-1-methylpyrrolidin-1-ium malate,
(2S)-2-(4,5-dimethylpyridin-3-yl)-1-methylpyrrolidin-1-ium malate,
(2S)-2-(4,6-dimethylpyridin-3-yl)-1-methylpyrrolidin-1-ium malate,
(2S)-2-(5,6-dimethylpyridin-3-yl)-1-methylpyrrolidin-1-ium malate,
(2S)-1-methyl-2-(4-methylpyridin-3-yl)pyrrolidin-1-ium salicylate,
(2S)-1-methyl-2-(2-methylpyridin-3-yl)pyrrolidin-1-ium salicylate,
(2S)-2-(2,4-dimethylpyridin-3-yl)-1-methylpyrrolidin-1-ium salicylate,
(2S)-2-(2,5-dimethylpyridin-3-yl)-1-methylpyrrolidin-1-ium salicylate,
(2S)-2-(2,6-dimethylpyridin-3-yl)-1-methylpyrrolidin-1-ium salicylate,
(2S)-2-(4,5-dimethylpyridin-3-yl)-1-methylpyrrolidin-1-ium salicylate,
(2S)-2-(4,6-dimethylpyridin-3-yl)-1-methylpyrrolidin-1-ium salicylate, and
(2S)-2-(5,6-dimethylpyridin-3-yl)-1-methylpyrrolidin-1-ium salicylate.

In various embodiments, a vaporizable alkaloid composition herein comprises from about 1 wt. % to about 20 wt. % of at least one substituted pyridine compound of Formula (I), or salt thereof, or mixed salt thereof, and more preferably from about 4 wt. % to about 12 wt. % of at least one substituted pyridine compound of Formula (I), or salt thereof, or mixed salt thereof, based on the total weight of the vaporizable alkaloid composition. In preferred embodiments, the amount of substituted pyridine compound of Formula (I) in a vaporizable alkaloid composition can be targeted to 100 mg/mL (w/v), recognizing that such a composition can always be diluted (even by the end user) with acceptable solvent (e.g. PG and/or VG) such that the actual composition an individual uses in an electronic device might have lesser amounts or alkaloid (w/v) than 100 mg/mL.

In more preferred embodiments, a vaporizable alkaloid composition herein comprises from about 4 wt. % to about 12 wt. % of (S)-2-methyl-5-(1-methylpyrrolidin-2-yl)pyridine, based on the total weight of the vaporizable alkaloid composition, and as added to the composition.

1a. Alternative Alkaloids

In other embodiments of the present disclosure, a vaporizable alkaloid composition herein comprises at least one substituted pyridine compound, or salt, or mixed salt thereof, according to Formula (II):

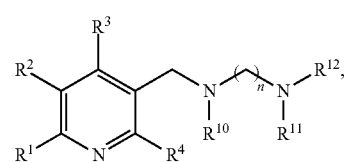

(II)

wherein $R^1$, $R^2$, $R^3$, $R^4$, $R^{10}$, $R^{11}$ and $R^{12}$ are independently selected from H, alkyl, substituted alkyl, cycloalkyl, substituted cycloalkyl, alkenyl, and substituted alkenyl; and n is an integer from 1 to 10.

In various embodiments, $R^{11}$ and $R^{12}$ are both H.
In various embodiments, $R^{11}$ is $CH_3$ and $R^{12}$ is H.
In various embodiments, $R^{11}$ and $R^{12}$ are both $CH_3$.
In various embodiments, n is an integer from 1 to 4.
Preferred $R^1$, $R^2$, $R^3$ and $R^4$ substituents follow the options delineated above for compounds of Formula (I).

In various examples, substituted pyridine compounds of Formula (II) for use in vaporizable alkaloid compositions of the present disclosure include, but are not limited to:

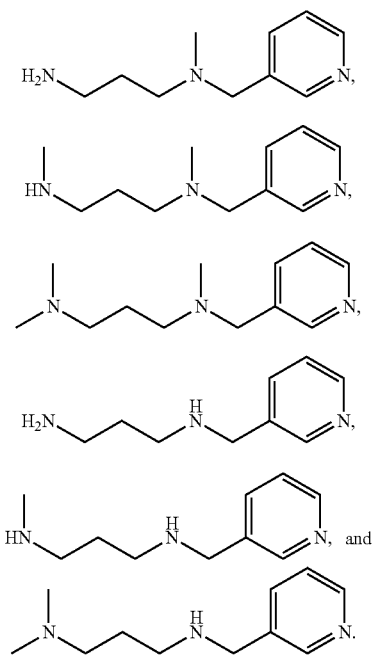

2. Chemosensory Irritant

Chemosensory irritants for use in vaporizable alkaloid compositions of the present disclosure include any natural, endogenous, phytochemical, or synthetic compound, including those derived from naturally occurring compounds by organic chemistry, capable of activating a TRP ion channel. Assays usable to determine whether a compound is indeed a TRP ion channel activator are found, for example, in H. P. Fallah, et al., "A Review on the Role of TRP Channels and Their Potential as Drug Targets: An Insight Into the TRP Channel Drug Discovery Methodologies," *Front. Pharmacol.*, 2022 13:914499.

Chemosensory irritants for use herein include, but are not limited to, oleocanthal, 4-hydroxy-2-nonenal, 4-oxo-2-nonenal, allicin, allyl isothiocyanate, icilin, polygodial, cinnamaldehyde, trans-p-methoxycinnamaldehyde, methyl syringate, 2-chlorobenzylidene malononitrile, 1-chloroacetophenone, ethyl bromoacetate, 4-hydroxyhexenal, toluene diisocyanate, p-benzoquinone, methyl p-hydroxybenzoate, flufenamic acid, niflumic acid, mefenamic acid, diclofenac, hydroxy-α-sanshool, 6-paradol, linalool, carvacrol, eugenol, thymol, vanillin, methyl eugenol, 2,6-dimethylphenol, 2,5-dimethylphenol, 3,4-dimethylphenol, 2,6-diisopropylphenol, caffeine, farnesyl thiosalicylic acid, 4-allylanisole, curcumin, niacin, camphor, olvanil, arvanil, anandamide (AEA), 2-AG, NADA, OLDA, PEA, NGABA, NGly, NAsp, NSer, $\Delta^9$-tetrahydrocannabinol ($\Delta^9$-THC), $\Delta^9$-THCA, $\Delta^9$-THCV, $\Delta^9$-THCVA, CBD, CBDA, CBDV, CBG, CBGA, CBGV, CBN, CBC, WIN55,212-2, AM630, (R)-AM1241, (S)-AM1241, SR141716A, Gp-1a, AM251, SR144528, JWH133, HU308, HU910, CP55,940, Nabilone, various phytochemicals from *Euphorbia reinifera, Euenia carophyllata, Ocimum gratissiumum, Panax, Aframomum melgueta, Evodia rutaecarpa, Drymis winteri, Cinnamosma fragrans, Warburgia, Scutellaria baicalensis, Vitex agnus, Pterodon pubescens, Croton macrostachyus, Angelicae pubescentis, Ephedra sinica, Amphilophium crucigerum, Bosewellia carterii, Commiphora myrrha, Echinophora platyloba, Nypa fruticans, Corydalis saxicola, Coptis chinensis, Ononis spinosa, Parkia platycephala,* and *Cymbopogon citratus,* and the entirety of a subset of chemosensory irritants separately defined as spice additives having a spiciness of from about 1,000 SHU to about 20,000,000 SHU. Many spice additives for use herein are phytochemicals found in various herbs and fruits, such as compounds from *Capsicum anmuum, Zingiber officiale,* and *Piper nigrum.*

In accordance with various embodiments, a spice additive for use as a chemosensory irritant in the vaporizable alkaloid compositions of the present disclosure is an organic compound having a spiciness or heat of about 1,000 to about 20,000,000 Scoville Heat Units (SHU), and more preferably from about 100,000 to about 20,000,000 Scoville Heat Units (SHU). Thus, a spice additive for purposes herein is a defined group of chemical compounds. Calculation of Scoville Heat Units can be found in American Spice Trade Associate (ASTA) 1985 Official Analytical Methods of the American Spice Trade Association, $3^{rd}$ ed., Amer. Spice Trade Assn., Englewood Cliffs, N.J.

In various embodiments, a spice additive herein comprises a capsaicinoid or mixture of capsaicinoids. In certain examples, a liquid extract comprises a mixture of capsaicinoids, having been prepared by solvent extraction of chili peppers known to contain mixtures of capsaicinoids rather than only capsaicin. In other embodiments, capsaicin is sourced and used.

In other examples, spice additives are used that are not chemically related to capsaicinoids, but nonetheless have measurable heat levels reported in Scoville units. These compounds are typically extracted from peppers other than chili peppers (*Capsicum annuum*), such as black pepper (*Piper nigrum* L.), with the most useful spice additive that is not a capsaicinoid being piperine (E, E, or trans-trans isomer). Other spice additives for use herein that are not capsaicinoids include, but are not limited to, Shogaol, gingerol, isopiperine, chavicine, isochavicine, 2-piperamine, piperanine (4,5-dihydropiperine), piperamide, 4-pipericide, piperyline, piperlonguminine, piperettine, piperdardine (6,7-dihydropiperettine), 5-sarmentodine, 6-sarmentine, and 7-trichostachine.

In various embodiments, a spice additive is selected from the group consisting of capsaicin, dihydrocapsaicin, norcapsaicin, nordihydrocapsaicin, homocapsaicin, homodihydrocapsaicin, gingerol, piperine, Shogaol, and mixtures thereof. Other capsaicinoids besides those six articulated may be used in the compositions herein, noting that it has been described that there are at least seven different capsaicinoids in the genus *Capsicum annuum* and perhaps two of them, likely capsaicin and dihydrocapsaicin, together are the capsaicinoids responsible for the spiciness of chili peppers. See M. D. Collins, et al., "Improved Method for Quantifying Capsaicinoids in *Capsicum* Using High-Performance Liquid Chromatography," *HortScience* 30(1):137-139, 1995. Although the above-referenced compounds fall in the general class of chemosensory irritants, it is convenient to group these compounds in the subset of chemosensory irritants defined as spice additives having a spiciness of from about 1,000 to about 20,000,000 Scoville Heat Units (SHU).

In various embodiments, a vaporizable alkaloid composition herein comprises from about 0.0001 wt. % to about 0.5 wt. % of a spice additive, based on the total weight of the vaporizable alkaloid composition, wherein the spice additive exhibits a spiciness or heat of about 1,000 to about 20,000,000 Scoville Heat Units (SHU). For spice additives having a spiciness of greater than about 10,000,000 SHU, this amount can be reduced considerably, such as from about 0.0001 wt. % to about 0.01 wt. % of a spice additive, based on the total weight of the composition.

In preferred embodiments, a vaporizable alkaloid composition herein comprises capsaicin ((E)-N-[(4-hydroxy-3-methoxyphenyl)methyl]-8-methylnon-6-enamide, CAS No.: 404-86-4). In a pure form (100% active), capsaicin is a white crystalline solid with a MP of 65° C. The purified material may be used directly in the compositions herein and is available, for example, from Sigma-Aldrich Co., VWR Avantor, and Alfa Chemistry, amongst other chemical suppliers.

In preferred embodiments, a vaporizable alkaloid composition herein comprises from about 0.0001 wt. % to about 0.01 wt. % capsaicin ((E)-N-[(4-hydroxy-3-methoxyphenyl)methyl]-8-methylnon-6-enamide), based on the total weight of the vaporizable alkaloid composition. In more preferred examples, the amount of capsaicin is from about 0.0005 wt. % to about 0.0015 wt. %, based on the total weight of the composition.

In various example, a "liquid capsaicin" is used in the vaporizable alkaloid compositions herein, such as for cost and practicality reasons. For example, Capsicum Flavor Extract can be used, which is available in gallon up to drum quantities from OliveNation, LLC, Avon, MA. This product is an ethanolic extract of chili peppers, having a clear reddish brown appearance and a specific gravity of about 0.8 g/mL at 20° C. This commercial material is about 99.1 wt. % ethanol and about 0.9 wt. % capsaicinoid actives.

In various embodiments, a vaporizable alkaloid composition herein comprises from about 0.05 wt. % to about 0.15 wt. % capsicum liquid (e.g., Capsicum Flavor Extract, from Olive Nation LLC, having about 0.9 wt. % active capsaicinoids), based on the total weight of the vaporizable alkaloid composition.

3. Solvents

In various embodiments, a vaporizable alkaloid composition herein comprises at least one solvent. Solvents in vaporizable compositions intended to be vaporized and inhaled by a human include, but are not limited to, propylene glycol, water, ethanol, glycerin, and mixtures thereof. As can be gleaned from the exemplary compositions herein, water might be entrained in compositions that comprise aqueous ethanol (e.g., 190 proof ethanol). Similarly, additional ethanol might be brought into a composition that utilizes a capsaicin liquid (e.g., capsaicinoids in ethanol).

In various embodiments, a vaporizable alkaloid composition herein comprises from about 85 wt. % to about 99.9 wt. % total solvent, based on the total weight of the vaporizable alkaloid composition. In certain examples, the solvent comprises a majority of vegetable glycerin, with smaller amounts of propylene glycol and ethanol (and trace water).

In various embodiments, a vaporizable alkaloid composition herein comprises a mixture of solvents including from about 85.0 wt. % to about 95.0 wt. % vegetable glycerin, based on the total weight of the composition and from about 0.5 wt. % to about 3 wt. % propylene glycol, based on the total weight of the composition. In certain examples, the amount of total solvent (regardless of composition) may be indicated as "quantity sufficient" or "q.s." which is that amount of solvent necessary to total a composition up to 100 wt. %.

4. Optional Flavoring Agents

In various embodiments, a vaporizable alkaloid composition herein may optionally comprise up to about 1.0 wt. % of at least one flavoring agent, based on the total weight of the composition. The wt. % of flavoring agent(s) used in a composition herein will vary widely based on the type of flavor and the desired sensory outcome, and in some instances, the amount used will be far less than 1.0 wt. %, (e.g., 0.1 wt. % or less). Optional flavoring agents for use herein include, but are not limited to, geraniol, geranial, valeric acid, methyl salicylate, ethyl maltol, ethyl butyrate, ethyl acetate, maltol, ethyl vanillin, ethyl 3-methyl-3-phenylglycidate, furaneol, methyl cyclopentenolone, methyl cyclopentenolone, ethyl cyclopentenolone, δ-decalactone, γ-decalactone, α-nonalactone, β-nonalactone, cis-3-hexanol, iso-amyl acetate, ethyl-2-methyl butyrate, butyric acid, ethyl butyrate, 2-methylbutyric acid, benzyl alcohol, ethyl hexanoate, benzaldehyde, iso-amyl isovalerate, hexanoic acid, ethyl propionate, γ-undecalactone, acetyl propionyl, raspberry ketone, furfural, 5-methylfurfural, maltol, 2-acetylpyrazine, 2,3,5-trimethylpyrazine, 2-acetylpyrrole, 2-isopropyl-4-methylthiazole, 2-isobutylthiazole, furfuryl mercaptan, thiomenthone, p-menthene-8-thiol, tropathiane, hexyl acetate and mixtures thereof.

Example Compositions

In various embodiments, a vaporizable alkaloid composition herein comprises at least one substituted pyridine compound of Formula (I), or a salt or mixed salt thereof and a chemosensory irritant in a suitable solvent. In various examples, the chemosensory irritant comprises a spice additive having a spiciness of about 1,000 to about 20,000,00 SHU. In various examples, the compositions further comprise at least one organic acid to convert at least some of the substituted pyridine compound of Formula (I) to its corresponding salt or mixed salt. The resulting compositions are thin, transparent and homogeneous liquids.

TABLE 1 provides general embodiments of vaporizable alkaloid compositions in accordance with the present disclosure.

TABLE 1

Vaporizable Alkaloid Compositions in General

| Ingredient | Weight Percent (wt. %) |
|---|---|
| Substituted pyridine compound of Formula (I)[1] | 1 wt. % to about 80 wt. % |
| Organic Acid[2] | 0.05 wt. % to about 1.5 wt. % |
| Chemosensory irritant[3] | 0.0001 wt. % to about 0.5 wt. % |
| Flavoring agent[4] | 0 to about 1 wt. % |
| Solvents[5] | q.s. |
| Total | 100.00 wt. % |

Note 1: Compositions according to Table 1 are designed to target certain w/v levels of substituted pyridine compound in the finished composition, such as for example, 1000 mg/mL, 750 mg/mL, 500 mg/mL, 250 mg/mL, or 100 mg/mL. As mentioned herein, the compositions of Table 1 having these relatively high levels of substituted pyridine compound (e.g., ≥100 mg/mL) can be considered concentrates and as such, may be diluted further by a third party manufacturer or compounder or even by an end user who may be refilling a refillable electronic device.

Note 2: In preferred compositions from Table 1, the molar ratio of substituted pyridine free base to total organic acid(s) $R^9$—$CO_2H$ is from about 25:1 to about 75:1, and more preferably about 50:1. Therefore, it is expected that the majority of the substituted pyridine compound of Formula (I) in any composition given the above-referenced weight percent ranges will remain as the free base, regardless of the molecular weights of the free base alkaloid(s) and the organic acid(s).

Note 3: In these compositions, a range of from about 0.0001 wt. % to about 0.01 wt. % is the preferred range for spice additives in the composition as standardized to capsaicin actives, whereas the wider range provided in Table 1, i.e., from about 0.0001 wt. % to about 0.5 wt. %, reflects a general range inclusive of any of the above-mentioned chemosensory irritants, including within the subset of spice additives that are not necessarily capsaicinoids. The amount of chemosensory irritant used in a vaporizable alkaloid composition can be adjusted in accordance with its measured TRP channel activator $EC_{50}$ or $[A]_{50}$ value, which is the molar concentration of an activator that produces 50% of the maximal possible effect of that activator. Charts of activators of human TRP receptors and their $EC_{50}$ values are available See, for example, L. Premkumar, "Transient Receptor Potential Channels as Targets for Phytochemicals," *ACS Chem. Neurosci.*, 5(11) 1117-1130, 2014, in conjunction with R. Neubig, et al., "International Union of Pharmacology Committee on Receptor Nomenclature and Drug Classification. XXXVIII. Update on Terms and Symbols in Quantitative Pharmacology," *Pharmacological Reviews*, 55(4), 597-606 (2003). The phytochemicals disclosed by Premkumar are incorporated herein by reference for their express use in vaporizable alkaloid composition of the present disclosure.

The amount of spice additive (in wt. %), when chosen as the chemosensory irritant, can be adjusted accordingly for spice additives having a lower or higher spiciness than capsaicin (< or >16,000,000 SHU). In other words, alternative spice additives to capsaicin can be standardized to capsaicin. As a rough estimate, the ratio of the SHU for an alternative spice additive to the SHU of capsaicin (16,000,000 SHU) can be used to calculate a reasonable amount of a different spice additive to use in place of capsaicin. For example, Shogaol (160,000 SHU) may be used at 100 times the 0.0001 wt. % to about 0.01 wt. % range preferred for active capsaicin (16,000,000 SHU) since the ratio of the Scoville numbers is 16,000,000 SHU/160,000 SHU=100. Therefore an appropriate range for Shogaol actives in a composition might be from 0.01 wt. % to about 1 wt. % Shogaol, based on the total weight of the composition. Less spice additive would be added if using a spice additive having a spiciness of greater than 16,000,000 SHU. Focus groups and sensory panels can of course help to refine these estimated ranges but being able to calculate in this way presents a starting point. The ability to interchange spice additives is particularly useful if there are supply/cost issues for a specific spice additive, or if certain users desire a different sensory experience. Additionally, if a liquid extract is used rather than active spice additive, such as liquid capsaicin, the wt. % of spice additive actives in the compositions of Table 1 is increased accordingly.

Note 4: In these compositions, flavoring agents are optional as these can be added, if desired at all, at a later time, such as if the compositions of Table 1 are diluted by a third party provider or by the end user who is capable of filling a refillable device. So for example, a composition according to Table 1 can begin unflavored and then a third party or end user may dilute that composition (e.g., with VG and/or PG) and add their own choice of flavoring agent.

Note 5: In these compositions, the solvents are chosen partly on the basis of being acceptable for inhalation since the composition will ultimately be used in an electronic device for vaping. Therefore, the solvents in Table 1 will typically be selected from the group consisting of propylene glycol, glycerin, ethanol, water, and mixtures thereof. Each composition may comprise a majority of propylene glycol, a majority of vegetable glycerin, or a mixture of these two as the majority of the solvent component. As mentioned, a third party or end user may dilute the compositions of Table 1 further, and may choose to use propylene glycol, vegetable glycerin, or mixtures thereof (e.g., 50/50 VG/PG) for this purpose. Of further note is that at higher levels of substituted pyridine compound(s) of Formula (I), such as greater than about 20 wt. %, solubility of the alkaloid may present a problem, in which case solvent ratios are adjusted to improve solubility, such as by increasing ethanol wt. % and decreasing glycerin and/or propylene glycol wt. %. In general, substituted pyridine compounds of Formula (I) are more likely to be more soluble in ethanol as compared to VG or PG. Compositions having from about 4 wt. % to about 12 wt. % substituted pyridine compounds of Formula (I) are generally homogeneous with mixtures of VG/PG and very little ethanol.

Table 2 sets forth embodiments of vaporizable alkaloid compositions according to the present disclosure. The compositions derive from the generalized embodiments presented in Table 1, where the chemosensory irritant is selected from the subset referred to as spice additives, and the notes above in reference to Table 1 and have been shown to be both vaporizable and consumer acceptable as presented in the table or after dilution to lower w/v alkaloid. The exemplary compositions in Table 2 are only examples and should not be considered to limit the scope of the present disclosure in any way. For example, other substituted pyridine compounds of Formula (I) may be used in place of (S)-2-methyl-5-(1-methylpyrrolidin-2-yl)pyridine, other organic acids may be used besides citric and acetic acids, and other chemosensory irritants besides a spice additive may be used to provide a perceivable throat hit. Further, changes to the relative amounts of solvents may be made to each composition to improve solubility.

TABLE 2

Exemplary Vaporizable Alkaloid Compositions

| Ingredient (wt. %) | Compositions (having 100 mg/mL alkaloid) | | | | |
| --- | --- | --- | --- | --- | --- |
| | 1 | 2 | 3 | 4 | 5 |
| (S)-2-methyl-5-(1-methylpyrrolidin-2-yl)pyridine | 7.93 | 7.93 | 7.93 | 7.93 | 7.93 |
| Citric Acid (food grade, crystals) | 0.12 | 0.12 | 0.12 | 0.12 | 0.12 |
| Acetic Acid (glacial, 99%) | 0.01 | 0.01 | 0.01 | 0.01 | 0.01 |
| Capsaicin (≥95%, crystalline solid) (16,000,000 SHU) | 0.001 | — | — | — | — |

TABLE 2-continued

Exemplary Vaporizable Alkaloid Compositions

| | Compositions (having 100 mg/mL alkaloid) | | | | |
|---|---|---|---|---|---|
| Ingredient (wt. %) | 1 | 2 | 3 | 4 | 5 |
| Capsicum Liquid Extract (0.9% active capsaicinoids in ethanol) | — | 0.10 | — | — | — |
| Shogaol (≥90%, CAS No.: 36752-54-2, solid) (160,000 SHU) | — | — | 0.10 | — | — |
| Piperine (≥97%, crystalline or powder) (100,000 SHU) | — | — | — | 0.16 | — |
| Gingerol (>98%, light yellow oil) (60,000 SHU) | — | — | — | — | 0.270 |
| Propylene glycol | 1.28 | 1.28 | 1.28 | 1.22 | 1.11 |
| Vegetable glycerin | 90.53 | 90.53 | 90.53 | 90.53 | 90.53 |
| Ethanol (190 Proof alcohol) | 0.129 | 0.03 | 0.03 | 0.03 | 0.03 |
| Total | 100.00 | 100.00 | 100.00 | 100.00 | 100.00 |

The numerical entries in Table 2 are ingredients "as added" and are rounded off.

As discussed herein, small amounts of alkaloid salt (in this case, (2S)-1-methyl-2-(6-methylpyridin-3-yl)pyrrolidin-1-ium salts) are expected to form from the presence of citric and acetic acids in the compositions, and it is not likely that any free citric or acetic acids will remain as free acids given the large molar excess of (S)-2-methyl-5-(1-methylpyrrolidin-2-yl)pyridine. Compositions 1-5 in Table 2 each comprise about 0.04 moles total organic acid and about 2.15 moles (S)-2-methyl-5-(1-methylpyrrolidin-2-yl)pyridine, giving a molar ratio of free base to organic acid of about 54:1.

For compositions that use 190 Proof alcohol rather than absolute alcohol, there will be a small amount of water in the composition that is not separately added, and thus is not noted since it is not "as added." Any composition showing 190 Proof alcohol as an ingredient can be converted to a composition incorporating absolute alcohol and water, if desired.

Compositions 1 and 2 simply represent two recipes to get to the same end result, with Composition 1 using ≥95%, crystalline solid capsaicin and Composition 2 using an ethanolic extract of capsaicinoids (i.e., *Capsicum* Liquid Extract, obtained from OliveNation, LLC). As mentioned, it is more convenient and cost effective to use a liquid capsaicin.

The entries in Table 2 demonstrate how other spice additives (Shogaol, piperine, and gingerol in these examples) can be used in place of capsaicin or capsaicinoids by adjusting the amount of the alternative spice additive based on its relative spiciness to capsaicin (in SHU). As mentioned, slight changes in solvents can be implemented to accommodate differences in solubilities for various spice additives. The compositions 1-5 are expected to have similar throat hit to users based on equalized spiciness in SHU between the compositions, but the personal experience may still be individualized based on a person's physiology and what they perceive.

Each example composition in Table 2 comprises about 100 mg/mL (S)-2-methyl-5-(1-methylpyrrolidin-2-yl)pyridine. It is important to note that these exemplary compositions can be adjusted such that the target w/v of (S)-2-methyl-5-(1-methylpyrrolidin-2-yl)pyridine in the composition is anywhere from about 1 mg/mL to about 1000 mg/mL. Target w/v include, but are not limited to, 1000 mg/mL, 750 mg/mL, 500 mg/mL, 250 mg/mL, and 100 mg/mL (as disclosed in Table 2). An advantage to producing concentrates, especially even a super concentrate having 1000 mg/mL total w/v of substituted pyridine compound, is reduction in the cost of transportation to manufacturers, compounders and retailers. Third party compounders or end users are expected to take any of these "concentrates," (e.g., 1000 mg/mL, 750 mg/mL, 500 mg/mL, 250 mg/mL, or 100 mg/mL) and dilute them down with PG, or VG or with blends of PG and VG, to substituted pyridine compound w/v targets that are <100 mg/mL, such as for example, 1 mg/mL, 3 mg/mL, 6 mg/mL, 9 mg/mL, 12 mg/mL, 15 mg/mL, 18 mg/mL, 21 mg/mL, 24 mg/mL, 27 mg/mL, 30 mg/mL, 33 mg/mL, 36 mg/mL, 39 mg/mL, 42 mg/mL, 45 mg/mL, 48 mg/mL, 51 mg/mL, 54 mg/mL, 57 mg/mL, 60 mg/mL, 63 mg/mL, 66 mg/mL, 69 mg/mL, 72 mg/mL, 75 mg/mL, 78 mg/mL, 81 mg/mL, 84 mg/mL, 87 mg/mL, 90 mg/mL, 93 mg/mL, 96 mg/mL, or 99 mg/mL.

Methods of Preparing Vaporizable Alkaloid Compositions

The vaporizable alkaloid compositions in Tables 1 and 2 may be prepared by a straightforward mixing of the ingredients shown in the tables in a laboratory vessel with magnetic or overhead stirring, or in a food industry mixer, followed by heating if necessary to obtain complete solubility and clarity. In preferred embodiments, premixes are first made and then combined.

In various embodiments, a first premix, indicated as Premix A, comprises propylene glycol, chemosensory irritant, such as a spice additive, organic acid, and 190 Proof alcohol. In some examples, there may be two or more organic acids in Premix A, and/or the PG may be replaced with VG or included with VG.

In various embodiments, a second premix, indicated as Premix B, comprises the desired substituted pyridine compound(s) of Formula (I) dissolved in a compatible solvent such as vegetable glycerin, propylene glycol, a 50/50 (v/v) blend of vegetable glycerin and propylene glycol, and/or ethanol. As mentioned, in order to reach highly concentrated compositions, such as those having >20 wt. % substituted pyridine compound(s) and finishing with >100 mg/mL substituted pyridine compound(s), other solvents may be required, such as ethanol.

In certain examples, Premix A is then combined with Premix B and the resulting mixture, if hazy, is heated at about 190° F. for about 1 hr., or until the mixture is entirely clear. Upon cooling, the mixture will remain clear, as it appears the compositions are thermodynamically stable.

Table 3 sets forth non-limiting examples of Premix A.

TABLE 3

Examples of Premix A

| Ingredient (wt. %) | Premix A | | | |
| --- | --- | --- | --- | --- |
|  | A1 | A2 | A3 | A4 |
| Propylene glycol | 82.98 | 77.04 | 73.44 | 67.04 |
| Capsaicin (≥95%, crystalline solid) | 0.06 | — | — | — |
| Shogaol (≥90%, CAS No.: 36752-54-2, solid) | — | 6.0 | — | — |
| Piperine (≥97%, crystalline or powder) | — | — | 9.6 | — |
| Gingerol (≥98%, light yellow oil) | — | — | — | 16.0 |
| Citric acid (crystals) | 7.77 | 7.77 | 7.77 | 7.77 |
| Glacial acetic acid | 0.84 | 0.84 | 0.84 | 0.84 |
| 190 Proof Alcohol | 8.35 | 8.35 | 8.35 | 8.35 |
| Total | 100.00 wt. % | 100.00 wt. % | 100.00 wt. % | 100.00 wt. % |

Table 4 sets forth non-limiting examples of Premix B.

TABLE 4

Examples of Premix B

| Ingredient (wt. %) | Premix B | | | |
| --- | --- | --- | --- | --- |
|  | B1 | B2 | B3 | B4 |
| (S)-2-methyl-5-(1-methylpyrrolidin-2-yl)pyridine | 8.0 | 20.0 | 40.0 | 80.0 |
| Vegetable glycerin | 92.0 | 80.0 | 35.0 | — |
| Ethanol (100% absolute) | — | — | 25.0 | 20.0 |
| Total | 100.00 wt. % | 100.00 wt. % | 100.00 wt. % | 100.00 wt. % |

In a non-limiting example where premixes are combined to produce a final vaporizable alkaloid composition having 100 mg/mL (S)-2-methyl-5-(1-methylpyrrolidin-2-yl)pyridine target, Premix A1 and Premix B1 are combined in the weight percentages set forth in Table 5, with the resulting mixture heated for about 1 hr. at 190° F.

TABLE 5

Vaporizable alkaloid composition having 100 mg/mL alkaloid target

| Ingredient (wt. %) | Final Conc. |
| --- | --- |
| Premix A1 | 1.54 |
| Premix B1 | 98.46 |
| Total | 100.00 wt. % |

One method to obtain final compositions having >100 mg/mL alkaloid is to prepare more concentrated versions of Premix B, as shown in Table 4 where the alkaloid is increased from Premix B1 through B4. Depending on the nature of the substituted pyridine compound of Formula (I) used in Premix B, and the desired concentration, solubility can become an issue. In those cases, the vegetable glycerin in Premix B is replaced, at least in part, by another solvent such as ethanol, as embodied by the examples in Table 4 when the substituted pyridine compound of Formula (I) is (S)-2-methyl-5-(1-methylpyrrolidin-2-yl)pyridine.

The above strategy of using Premix A and Premix B, where the substituted pyridine compound of Formula (I) is (S)-2-methyl-5-(1-methylpyrrolidin-2-yl)pyridine, can be reliably used to reach up to about 225 mg/mL to about 250 mg/mL w/v (S)-2-methyl-5-(1-methylpyrrolidin-2-yl)pyridine in a final concentrated vaporizable alkaloid composition. To exceed about 250 mg/mL w/v (S)-2-methyl-5-(1-methylpyrrolidin-2-yl)pyridine in a final composition does require a change in solvent to Premix B from entirely vegetable glycerin to a mixture of solvents comprising at least some ethanol.

Methods of Use

1. Smoking Cessation Through Vaping Vaporizable Alkaloid Compositions

The vaporizable alkaloid compositions in accordance with the present disclosure, or dilutions thereof, are intended to be dispensed from an electronic device, such as an e-cigarette, in the form of a vapor that a user can inhale as if smoking a traditional tobacco product like a cigarette.

As mentioned herein above, one goal of the present disclosure is to provide vaporizable alkaloid compositions and progressive dilutions thereof to a smoker engaged in a smoking cessation program.

In various embodiments, a method of smoking cessation comprises administering to an individual desirous of cessation a series of vaporizable alkaloid compositions over a time period determined for cessation, each vaporizable alkaloid composition in the series comprising at least one substituted pyridine compound, or salt or mixed salt thereof, having Formula (I):

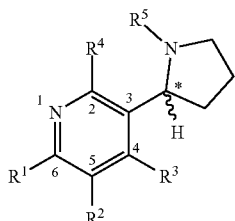

(I)

wherein R¹, R², R³, and R⁴ are independently selected from H, alkyl, cycloalkyl, and alkenyl, with the proviso that R¹, R², R³, and R⁴ cannot all be H;

wherein each of the vaporizable alkaloid compositions in the series comprises decreasing (w/v) amounts of said substituted pyridine compound, or salt, or mixed salt thereof;

wherein the individual desirous of cessation progresses through each of the compositions in the series in decreasing order of (w/v) amounts of said substituted pyridine compound, or salt, or mixed salt thereof; and wherein the individual desirous of cessation uses each of said compositions by vaporizing and inhaling each composition from an electronic device over the time period determined for cessation.

In various embodiments, the individual desirous of cessation is a tobacco smoker who wants to stop smoking.

In various embodiments, the time period determined for cessation may be days, weeks, months or years in length, preferably several months to a year in length.

In various embodiments, the time period determined for cessation is part of a cessation program that further includes dispensation of the series of vaporizable alkaloid compositions over the time period determined for cessation.

In various embodiments, the time period determined for cessation is divided into consecutive time periods of shorter duration, wherein during each one of the shorter time periods the individual desirous of cessation receives and uses a different vaporizable alkaloid composition in place of tobacco smoking. In preferred embodiments, in each consecutive time period of shorter duration, the individual desirous of cessation receives a vaporizable alkaloid composition having progressively decreasing amounts of alkaloid in (w/v) units.

In various embodiments, the series of vaporizable alkaloid compositions comprises individual compositions as set forth in Table 6. This exemplary series of vaping liquids can be administered over the course of a 25 week cessation program. The table demonstrates that an individual receives a new vaping composition having lesser amounts of substituted pyridine compound for each week of the cessation program. At the end of the program, the individual desirous of cessation will be vaping a vaporizable alkaloid composition devoid of alkaloid.

TABLE 6

Series of vaporizable alkaloid compositions for a cessation program

| Program Week | Vaping Liquid | (mg/mL) alkaloid[1] |
|---|---|---|
| 1 | P1 | 100[2] |
| 2 | P2 | 95 |
| 3 | P3 | 90 |
| 4 | P4 | 85 |
| 5 | P5 | 80 |
| 6 | P6 | 75 |
| 7 | P7 | 70 |
| 8 | P8 | 65 |
| 9 | P9 | 60 |
| 10 | P10 | 55 |
| 11 | P11 | 50 |
| 12 | P12 | 45 |
| 13 | P13 | 40 |
| 14 | P14 | 35 |
| 15 | P15 | 30 |
| 16 | P16 | 24 |
| 17 | P17 | 21 |
| 18 | P18 | 18 |
| 19 | P19 | 15 |
| 20 | P20 | 12 |
| 21 | P21 | 9 |
| 22 | P22 | 6 |
| 23 | P23 | 3 |
| 24 | P24 | 1 |
| 25 | P25 | 0 |

Note 1:
The alkaloid in compositions P1-P25 comprises any substituted pyridine compound of Formula (I), or salts thereof, or mixed salts thereof. In preferred examples, the alkaloid in compositions P1-P25 comprises (S)-2-methyl-5-(1-methylpyrrolidin-2-yl)pyridine, or salts thereof, or mixed salts thereof. In more preferred examples, compositions P1-P25 consist of Composition 1 (or 2) from Table 2 and dilutions therefrom.

Note 2:
For a program that utilizes compositions comprising (S)-2-methyl-5-(1-methylpyrrolidin-2-yl)pyridine, P1 can be any of the compositions exemplified in Table 2 (each targeted to 100 mg/mL (S)-2-methyl-5-(1-methylpyrrolidin-2-yl)pyridine), and preferably Composition 1 (or 2). For compositions P2 through P25, P1 is diluted accordingly with VG and/or PG as mentioned, with flavoring agents added as needed and adjusted based on an individual's preferences.

In various embodiments, an individual enrolled in a smoking cessation program will check in with their program manager on a regular basis, such as weekly, for personal consultation and to receive a new and further diluted vaping liquid. At these regular check-ins, an assessment can be made as to the individual's compliance with the program, and adjustments made accordingly. Some changes to a program may be to keep an individual on a certain w/v level of alkaloid for a longer period of time than a week, or to change or adjust flavoring agents. Other changes can be made to vaping compositions in a series, such as changing between spice additives, or adding more or less spice additive to adjust throat hit sensed by the individual vaping the compositions provided. In certain examples, a liquid composition is provided to the individual, and the individual places the composition into the reservoir of his/her own refillable electronic device, such as a refillable e-cigarette. In other examples, a disposable (closed) device is provided to the individual, the device having been prefilled with a particular composition.

In various embodiments, an individual who has reached the end of the program will be vaping just flavored solvent containing no alkaloid. At this point it is expected the individual will not be smoking traditional tobacco products at all and may choose to stop vaping entirely.

In various embodiments, a method of vaping comprises vaporizing and inhaling a composition according to present disclosure from a disposable (closed) or a refillable (open) electronic device. In certain embodiments, the electronic device comprises an e-cigarette.

2. Alkaloid Dispensing Pouches for Oral Use

In various embodiments, versions of vaporizable alkaloid compositions in accordance with the present disclosure also find use in the manufacture of "alkaloid dispensing pouches." A pouch for oral use comprises a relatively small (e.g., 0.5 in×0.75 in) saliva-permeable fabric material enclosure containing a powder sealed therein, capable of releasing an alkaloid active into the oral cavity of an individual when the pouch is placed sublingually or in the buccal cavity of the individual. An alkaloid dispensing pouch according to the present disclosure is configured to release an alkaloid of Formula (I), or in alternative embodiments, release an alkaloid of Formula (II) over time. In some embodiments, release of alkaloid into the oral cavity of an individual from an alkaloid dispensing pouch may be characterized as "time release."

In various embodiments, an alkaloid dispensing pouch comprises a saliva-permeable nonwoven fabric and a powdered alkaloid composition sealed therein. In certain examples, the powdered alkaloid composition sealed within the pouch comprises a vaporizable alkaloid composition according to the present disclosure adsorbed onto a carrier or mixture of carriers such that it takes on the physical form of a powder or granulate. In other embodiments, a powdered alkaloid composition within an alkaloid dispensing pouch comprises a substituted pyridine compound according to either Formula (I) or (II), a solvent, and a carrier, wherein the mixture of alkaloid and solvent are adsorbed onto the carrier.

2a. General Embodiments of Alkaloid Dispensing Pouches

In general embodiments, an alkaloid dispensing pouch adapted for release of an alkaloid therefrom into the oral cavity of an individual, comprises:
  a saliva-permeable nonwoven fabric defining an enclosure containing an alkaloid composition therein, said alkaloid composition comprising:
  at least one substituted pyridine compound, or salt, or mixed salt thereof, according to Formula (I):

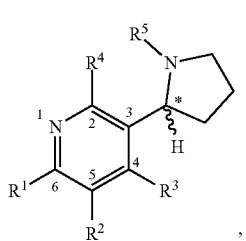

wherein $R^1$, $R^2$, $R^3$, $R^4$, and $R^5$ are independently selected from H, alkyl, substituted alkyl, cycloalkyl, substituted cycloalkyl, alkenyl, and substituted alkenyl, with the proviso that if $R^5$ is $CH_3$, then $R^1$, $R^2$, $R^3$, and $R^4$ cannot all be H; and
  a carrier, wherein the alkaloid dispensing pouch is entirely devoid of devoid of (R) or (S) nicotine.

In various embodiments, the alkaloid composition is an admixture of a substituted pyridine compound of Formula (I), in either solid or oil physical form, and the carrier.

In various embodiments, the alkaloid composition further comprises a solvent, such that the alkaloid composition can be adsorbed onto the carrier to form a powdered or granular composition that can be filled into said enclosure. In certain examples, the solvent is selected from the group consisting of propylene glycol, vegetable glycerin, water, ethanol, and mixtures thereof.

In various embodiments, the carrier comprises microcrystalline cellulose.

In various embodiments, the substituted pyridine compound according to Formula (I) comprises (S)-2-methyl-5-(1-methylpyrrolidin-2-yl)pyridine.

In alternative general embodiments, an alkaloid dispensing pouch adapted for release of an alkaloid therefrom into the oral cavity of an individual, comprises:
  a saliva-permeable nonwoven fabric defining an enclosure containing an alkaloid composition therein, said alkaloid composition comprising:
  at least one substituted pyridine compound, or salt, or mixed salt thereof, according to Formula (II):

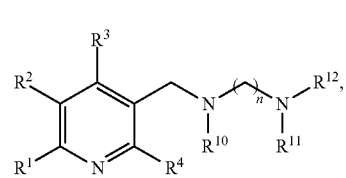

wherein $R^1$, $R^2$, $R^3$, $R^4$, $R^{10}$, $R^{11}$ and $R^{12}$ are independently selected from H, alkyl, substituted alkyl, cycloalkyl, substituted cycloalkyl, alkenyl, and substituted alkenyl; and n is an integer from 1 to 10; and
  a carrier, wherein the alkaloid dispensing pouch is entirely devoid of devoid of (R) or (S) nicotine.

In various embodiments, the alkaloid composition is an admixture of a substituted pyridine compound of Formula (II), in either solid or oil physical form, and the carrier.

In various embodiments, the alkaloid composition further comprises a solvent, such that the alkaloid composition can be adsorbed onto the carrier to form a powdered or granular composition that can be filled into said enclosure. In certain examples, the solvent is selected from the group consisting of propylene glycol, vegetable glycerin, water, ethanol, and mixtures thereof.

In various embodiments, the carrier comprises microcrystalline cellulose.

In various embodiments, the substituted pyridine compound according to Formula (II) comprises 3-[N-methyl-N-(3-aminopropyl)]aminomethylpyridine.

In various embodiments, an alkaloid dispensing pouch adapted for release of an alkaloid therefrom into the oral cavity of an individual, comprises:
  a saliva-permeable nonwoven fabric defining an enclosure containing an alkaloid composition therein, said alkaloid composition comprising a vaporizable alkaloid composition adsorbed onto a carrier, said vaporizable alkaloid composition comprising:
  at least one substituted pyridine compound of Formula (I), or salt or mixed salt thereof;

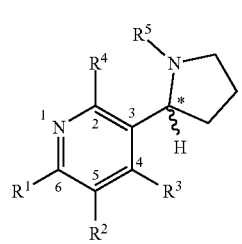

wherein $R^1$, $R^2$, $R^3$, $R^4$, and $R^5$ are independently selected from H, alkyl, substituted alkyl, cycloalkyl, substituted cycloalkyl, alkenyl, and substituted alkenyl, with the proviso that if $R^5$ is $CH_3$, then $R^1$, $R^2$, $R^3$, and $R^4$ cannot all be H;
    at least one chemosensory irritant;
    at least one solvent; and,
    optionally, at least one flavoring agent, wherein the alkaloid dispensing pouch is entirely devoid of devoid of (R) or (S) nicotine.

In certain examples, a chosen vaporizable alkaloid composition in accordance with the present disclosure is adsorbed onto a carrier such as microcrystalline cellulose such that the resulting material for the pouch is in the physical form of a powder or granulate.

Details of chemosensory irritants such as spice additives, solvents, and optional flavoring agents are found herein above under the general description of "vaporizable alkaloid composition."

2b. Saliva-Permeable Fabric for Pouches

Pouch material for use herein is chosen for its insolubility in water and for its permeability to water and saliva. Material is sized such that a filled pouch is appropriate for sublingual or buccal placement for extended periods of time. Subjectively, an alkaloid dispensing pouch is configured for comfortable mouth feel, including size of the filled and sealed pouch and texture of the pouch fabric.

Pouch material for use herein may be constructed from any number of various water-insoluble nonwoven materials, called "fabrics". Nonwoven fabrics, with their multitude of uses, are well known to those skilled in textiles. Nonwovens are described very thoroughly in "Nonwoven Fabrics: Raw Materials, Manufacture, Applications, Characteristics, Testing Processes," editors W. Albrecht, H. Fuchs and W Kittelmann, Wiley-VCH Verlag GmbH & Co. KgaA Weinheim, 2003. Such material can be prepared by forming a web of continuous filament and/or staple fibers and optionally bonding these fibers at fiber-to-fiber contact points to provide fabrics with the desired properties. The term "bonded nonwoven fabric" is used to include nonwoven fabrics where a major portion of the fiber-to-fiber bonding is achieved by either thermal fusion of adjacent fibers, or adhesive bonding that is accomplished through incorporation of adhesives in the web to "glue" fibers together, or by other bonding such as obtained by the use of liquid or gaseous bonding agents (usually in conjunction with heating) to render the fibers cohesive. Chemical bonding may be accomplished through the use of adhesive or latex powders dispersed between the fibers in the web, which is then activated by heat, ultraviolet or infrared radiation, or other suitable activation method. Thermally and chemically bonded carded webs are described in U.S. Pat. No. 6,689,242 to Bodaghi, the subject matter of which is incorporated herein. Thermally and/or chemically bonded nonwovens may be used as the pouch material herein. Powder bonding is a dry process that starts with the carding of staple fibers to form a fibrous web, which is then treated with powdered thermal plastic adhesive or latex materials and subjected to a series of ovens and calendar rolls to produce the nonwoven.

Nonwovens may also comprise fibers known as "bi-component fibers", for example "sheath/core bi-component fibers", which are fibers having an outer sheath area or layer with a lower melting point than the inner core area, allowing for efficient and controlled thermal bonding through melting of just the outer layer of each fiber. That is, the outer surface of a bi-component fiber can be made to have a lower melting point than the core of the fiber. For example, binder bi-component fibers where one component has adhesive properties under bonding conditions are widely employed to provide integrity to fibrous webs used as absorbents in personal care products or in filtration products. Additionally, multi-component fibers are similarly known and commercially incorporated into nonwovens. Examples of Such multi-component fibers are described in U.S. Pat. No. 5,382,400 (Pike et al.) and U.S. Pat. No. 5,866,488 (Terada et al.) and incorporated herein in their entireties.

During the bonding of the fibers, the web may be simultaneously subjected to mechanical compression to obtain the desired bonding, weights and thicknesses in a process known as "thermal compression bonding." Thermal compression bonding may be accomplished by using a hot embossing roll and a heat flat calendar roll and incorporating a method in which a heat treating machine such as a hot blast-circulating type, a hot through-air type, an infrared heater type or a vertical hot blast-blowing type is used to carry out thermal compression bonding. Mechanical compression may be used to set the loft or thickness of fabrics with similar basis weights. Normally, increasing the basis weight, or the mass per square area increases thickness, and increasing bonding and compression, decreases loft.

Nonwoven webs may be formed from a number of processes, for example, melt-blown, spun-bonded or spun-laid, toe-opened, wet-laid, air-laid, carded, and high pressure hydro-entangled. The basis weight of nonwoven webs is usually expressed in ounces of material per square yard (osy) or grams per square meter (gsm) and the fiber diameters are usually expressed in microns, or in the case of staple fibers, "denier." Denier is defined as grams per 9000 meters of fiber length. For a fiber having circular cross-section, denier may be calculated as fiber diameter in microns squared, multiplied by the density in grams/cc, multiplied by 0.00707. A lower denier indicates a finer fiber and a higher denier indicates a thicker or heavier fiber. The "mean fiber denier" is the sum of tile deniers for each fiber, divided by the number of fibers. A distribution of deniers or an "average fiber denier" refers to a distribution of fiber diameters around a specific value As used herein, the term "bulk density" refers to the weight of a material per unit of volume and usually is expressed in units of mass per unit of bulk volume (e.g., grams per cubic centimeter). Nonwovens may be produced by fibers having a single average value of diameters or denier, or two or more average value diameter fibers may be used together. For example, two or more distributions of fiber deniers may be combined into separate fiber webs (2½ denier and 4 denier fibers carded together for example). Then separate fiber webs may be laminated together. For example, a single nonwoven may comprise 2½, 4, 6, and 15 denier fibers, meaning it was constructed with four separate denier fibers (four separate average diameters of fibers "Spun-bonded fibers" refers to fibers formed by extrusion of molten thermoplastic material as filaments, described for example in U.S. Pat. No. 4,340,563 to Appel; U.S. Pat. No. 3,692,618 to Dorschner; U.S. Pat. No. 3,802,817 to Matsuki; U.S. Pat. Nos. 3,338,992 and 3,341,394 to Kinney, U.S. Pat. No. 3,502,763 to Hartman; U.S. Pat. No. 3,542,615 to Dobo; and, U.S. Pat. No. 5,382,400 to Pike, the entire contents of each incorporated herein by reference. Spun-bond fibers are generally not tacky when they are deposited onto a collecting surface. Spun-bond fibers are generally continuous and have average diameter from about 7 microns to about 60 microns, and most often between about 15 and 25 microns.

"Melt-blown" refers to fibers formed by extruding molten thermoplastic material through a plurality of fine, normally circular, die capillaries as molten threads or filaments into converging high velocity, usually hot, gas/air streams that attenuate the filaments of molten thermoplastic material to reduce their diameter, which may end up at micro-fiber diameter. Thereafter, the melt-blown fibers are carried by tile high velocity gas stream and are deposited on a collecting surface to form a web of randomly dispersed fibers. Such a process is disclosed, for example, in U.S. Pat. No. 3,849,241 (Butin et al.). Melt-blown fibers are micro-fibers that may be continuous or discontinuous and are generally smaller than 10 microns in average diameter and are generally tacky when deposited onto a collecting surface.

"Air-laid" is a well-known process by which a fibrous nonwoven layer can be formed In the air-laid process, bundles of small fibers having typical lengths of from about 3 to about 52 millimeters are separated and entrained in an air supply and deposited onto a forming screen, usually with the assistance of a vacuum. The randomly deposited fibers then are bonded to one another using, for example, hot air to activate a binder component or latex adhesive. The air-laying process is taught in, for example, U.S. Pat. No. 4,640,810 to Laursen and U.S. Pat. No. 5,885,516 to Christensen.

The preferred fibers incorporated in pouch fabric for use herein may be single-, bi- (e.g., sheath/core), or multi-component fibers, made from; poly-olefins such as polypropylene, polyethylene; various polyesters such as poly(ethylene terephthalate)-PET, poly(butylene terephthalate)-PBT or poly(trimethylene terephthalate)-PTT, polycarbonates, or polybutyrates and file like, viscose rayon, various polyamides such as nylons; polyacrylates, and, modacrylics, and mixtures of these types of polymers. In various preferred examples, viscose is used as the saliva-permeable nonwoven pouch fabric for alkaloid dispensing pouches herein.

Filling and sealing methods for pouches comprising nonwoven fabrics are disclosed in US Patent Application Publication US 2023/0211907, published Jul. 6, 2023 and assigned to Swedish Match North Europe AB, incorporated herein by reference. In various embodiments, an alkaloid dispensing pouch herein comprises a fill weight of an alkaloid composition (dry powder or granulate) of from about 100 mg to about 500 mg, preferably about 200 mg to about 400 mg. An upper limit is reached when pouches no longer fit comfortably sublingually or within the buccal cavity. Since the weight of the small piece of nonwoven fabric is negligible compared to the weight of an individual pouch, the fill weight of an alkaloid dispensing pouch herein is from about 100 mg to about 500 mg dry powdered or granulated alkaloid composition per pouch.

In various embodiments, an alkaloid dispensing pouch measures from about 0.12 inches to about 0.50 inches in width (or diameter) and from about 0.25 to about 0.75 inches in height. In some examples, a pouch may look like a small pillow (square, for example), or more like a capsule 2c. Powdered Fill Compositions for Alkaloid Dispensing Pouches In various embodiments, alkaloid dispensing pouches herein comprise a powdered or granular composition further comprising an alkaloid admixed with a carrier or a liquid alkaloid composition adsorbed onto a carrier. Either route is intended to result in a dry powdered or granulated alkaloid fill material to seal inside a nonwoven fabric enclosure.

The vaporizable alkaloid compositions for use in alkaloid dispensing pouches are amply described herein above Any of the compositions having a range of from about 1 mg/mL up to about 1000 mg/mL of substituted pyridine compound of Formula (I) or Formula (II) may be used. The chosen liquid composition is then adsorbed onto a suitable carrier, and this resulting powder or granulate is used as the fill material for each pouch.

Carriers for use herein include, but are not limited to, agar, agarose, albumin, alginate, casein, chitin, chondroitin, dextrin, fibroin, fucoidans, galactans, gellan, guar, scleroglucan, pullulan, xyloglucan, pectin, xanthan, psyllium, silica gel, fumed silica, magnesium aluminum silicates, clay, bentonite, hectorite, mesoporous silica, cellulose, cellulose acetate, hyaluronan, various elastin-like polypeptides, β-cyclodextrin, collagen, gelatin, chitosan, carrageenan, polylactic acid, polyglycolic acid, poly(lactic-glycolic acid) (PLGA), poly (2-hydroxyethyl methacrylate), poly(2-hydroxypropyl methacrylate), poly(acrylic acid), carboxymethyl cellulose, carboxyethyl cellulose, hydroxyethyl cellulose, hydrophobically-modified hydroxyethyl cellulose, hydroxypropyl cellulose, hydroxypropyl methyl cellulose, methyl cellulose, ethyl cellulose, microcrystalline cellulose, nitrocellulose, polyvinyl alcohol, polyvinylpyrrolidone, polyvinylmethacrylate, carboxyvinyl polymers, polyvinylacetate, polyvinyl co-polymers, various starches, modified starches, and combinations thereof. See, S. M. Fijul Kabir, et al., "Cellulose-based hydrogel materials: chemistry, properties and their prospective applications," *Prog. Biomater.*, 7, 153-174 (2018).

Carriers may be chosen on the basis of absorptive capacity and, to a lesser extent, taste. In instances where a carrier does not dissolve at all in the saliva present in the oral cavity, taste will not be a factor, and it is unlikely any insoluble carrier will pass between fibers of a nonwoven In other examples, a carrier may be soluble, and will pass through the porous pouch fabric along with the alkaloid composition. In preferred embodiments, a carrier comprises microcrystalline cellulose.

Tables 7, 8 and 9 set forth general embodiments of alkaloid compositions usable as fill material for alkaloid dispensing pouches of the present disclosure.

TABLE 7

Fill Compositions for Alkaloid Dispensing Pouches: Dry admixture

| Ingredient (wt. %) | Wt.% |
|---|---|
| Substituted pyridine compound of Formula (I) or Formula (II) | from 0.1 wt. % to 99.9 wt. % |
| Filler (e.g., microcrystalline cellulose) | from 0.1 wt. % to 99.9 wt. % |
| Total | 100.00 wt. % |

TABLE 8

Fill Compositions for Alkaloid Dispensing Pouches: Liquid Adsorption

| Ingredient (wt. %) | Wt. % |
|---|---|
| Alkaloid composition (comprising from 1 mg/mL to 1000 mg/mL w/v substituted pyridine compound of Formula (I) or (II) in a suitable solvent) | from 0.1 wt. % to 15 wt. % |
| Filler (e.g., microcrystalline cellulose) | from 85 wt. % to 99.9 wt. % |
| Total | 100.00 wt. % |

TABLE 9

Fill Compositions for Alkaloid Dispensing Pouches: Liquid Adsorption

| Ingredient (wt. %) | Wt. % |
|---|---|
| Vaporizable alkaloid composition (1 mg/mL to 1000 mg/mL w/v alkaloid) | from 0.1 wt. % to 15 wt. % |
| Filler (e.g., microcrystalline cellulose) | from 85 wt. % to 99.9 wt. % |
| Total | 100.00 wt. % |

Each of the resulting fill compositions from Tables 7, 8 or 9 are in the physical form of a dry powder or granulate. The resulting material is filled into nonwoven pouches at fill levels of from about 100 mg to about 500 mg dry powdered or granulated alkaloid composition per pouch and subsequently sealed to make individual alkaloid dispensing pouches for oral use.

In the detailed description, references to "various embodiments," "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected, coupled or the like may include permanent (e.g., integral), removable, temporary, partial, full, and/or any other possible attachment option. Any of the components may be coupled to each other via friction, snap, sleeves, brackets, clips or other means now known in the art or hereinafter developed. Additionally, any reference to without contact (or similar phrases) may also include reduced contact or minimal contact.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

All structural, chemical, and functional equivalents to the elements of the above-described various embodiments that are known to those of ordinary skill in the art are expressly incorporated herein by reference and are intended to be encompassed by the present claims. Moreover, it is not necessary for an apparatus or component of an apparatus, or method in using an apparatus to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No. claim element is intended to invoke 35 U.S.C. 112 (f) unless the element is expressly recited using the phrase "means for." As used herein, the terms "comprises", "comprising", or any other variation thereof, are intended to cover a non-exclusive inclusion, such that a chemical, chemical composition, process, method, article, or apparatus that comprises a list of elements does not include only those elements but may include other elements not expressly listed or inherent to such chemical, chemical composition, process, method, article, or apparatus.

The invention claimed is:

1. A vaporizable alkaloid composition, comprising:
   at least one substituted pyridine compound of Formula (I), or salt or mixed salt thereof;

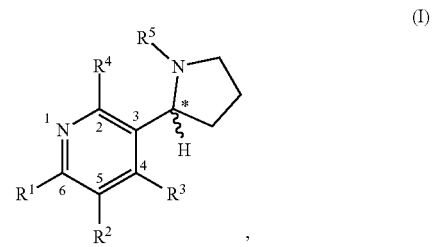

(I)

wherein $R^5$ is $CH_3$, and $R^1$, $R^2$, $R^3$, and $R^4$ are independently selected from alkyl, H, substituted alkyl, cycloalkyl, substituted cycloalkyl, alkenyl, and substituted alkenyl, with the proviso that at least one of $R^1$, $R^2$, $R^3$, and $R^4$ is not H,
   at least one organic acid,
   wherein the vaporizable alkaloid composition is entirely devoid of (R) or(S) nicotine and the molar ratio of substituted pyridine compound to organic acid is about 25:1 to about 75:1.

2. The vaporizable alkaloid composition of claim 1, wherein the substituted pyridine compound, or salt thereof, or mixed salt thereof, is selected from (R) or(S)-2-methyl-3-(1-methylpyrrolidin-2-yl) pyridine, (R) or(S)-4-methyl-3-(1-methylpyrrolidin-2-yl) pyridine, (R) or(S)-3-methyl-5-(1-methylpyrrolidin-2-yl) pyridine, (R) or(S)-2-methyl-5-(1-methylpyrrolidin-2-yl) pyridine, (R) or(S)-2,6-dimethyl-3-(1-methylpyrrolidin-2-yl) pyridine, (R) or(S)-2,4-dimethyl-5-(1-methylpyrrolidin-2-yl) pyridine, (R) or(S)-2,3-dimethyl-5-(1-methylpyrrolidin-2-yl) pyridine, (R) or(S)-2,4-dimethyl-3-(1-methylpyrrolidin-2-yl) pyridine, (R) or(S)-2,5-dimethyl-3-(1-methylpyrrolidin-2-yl) pyridine, and (R) or(S)-3,4-dimethyl-5-(1-methylpyrrolidin-2-yl) pyridine.

3. The vaporizable composition of claim 2, wherein the molar ratio of moles of(S)-2-methyl-5-(1-methylpyrrolidin-2-yl) pyridine to total moles of organic acid is about 50:1.

4. The vaporizable composition of claim 2, wherein the (w/v) concentration of(S)-2-methyl-5-(1-methylpyrrolidin-2-yl) pyridine in the vaporizable alkaloid composition is from about 1 mg/mL to about 1,000 mg/mL.

5. The vaporizable composition of claim 2, wherein the (w/v) concentration of(S)-2-methyl-5-(1-methylpyrrolidin-2-yl) pyridine in the vaporizable alkaloid composition is about 100 mg/mL.

6. The vaporizable alkaloid composition of claim 1, wherein the substituted pyridine compound, or salt thereof, or mixed salt thereof, is(S)-2-methyl-5-(1-methylpyrrolidin-2-yl) pyridine.

7. The vaporizable alkaloid composition of claim 1, wherein the at least one substituted pyridine compound of Formula (I), or salt thereof, or mixed salt thereof, consists of a mixture of(S)-2-methyl-3-(1-methylpyrrolidin-2-yl) pyridine free base and (2S)-1-methyl-2-(6-methylpyridin-3-yl) pyrrolidin-1-ium citrate/acetate mixed salts.

8. The vaporizable alkaloid composition of claim 1, further comprising at least one chemosensory irritant.

9. The vaporizable alkaloid composition of claim 8, wherein the at least one chemosensory irritant is selected from the group consisting of oleocanthal, 4-hydroxy-2-nonenal, 4-oxo-2-nonenal, allicin, allyl isothiocyanate, icilin, polygodial, cinnamaldehyde, trans-p-methoxycinnamaldehyde, methyl syringate, 2-chlorobenzylidene malononitrile, 1-chloroacetophenone, ethyl bromoacetate, 4-hydroxyhexenal, toluene diisocyanate, p-benzoquinone, methyl p-hydroxybenzoate, flufenamic acid, niflumic acid, mefenamic acid, diclofenac, hydroxy-a-sanshool, 6-paradol, linalool, carvacrol, eugenol, thymol, vanillin, methyl eugenol, 2,6-dimethylphenol, 2,5-dimethylphenol, 3,4-dimethylphenol, 2,6-diisopropylphenol, caffeine, farnesyl thiosalicylic acid, 4-allylanisole, curcumin, niacin, camphor, olvanil, arvanil, anandamide, cannabidiol, A9-tetrahydrocannabinol, baicalein, baicalin, wogonin, norwogonin, oroxylin A, B-sitosterol and mixtures thereof.

10. The vaporizable alkaloid composition of claim 8, wherein the chemosensory irritant is a spice additive exhibiting a spiciness of from about 1,000 to about 20,000,000 Scoville Heat Units (SHU).

11. The vaporizable alkaloid composition of claim 10, wherein the spice additive is selected from the group consisting of capsaicin, dihydrocapsaicin, norcapsaicin, nordihydrocapsaicin, homocapsaicin, homodihydrocapsaicin, gingerol, piperine, Shogaol, isopiperine, chavicine, isochavicine, 2-piperamine, piperanine (4,5-dihydropiperine), piperamide, 4-pipericide, piperyline, piperlonguminine, piperettine, piperdardine (6,7-dihydropiperettine), 5-sarmentodine, 6-sarmentine, 7-trichostachine, and mixtures thereof.

12. The vaporizable alkaloid composition of claim 11, wherein the spice additive is capsaicin or a mixture of capsaicinoids.

13. The vaporizable composition of claim 10, wherein the spice additive comprises capsaicin.

14. The vaporizable alkaloid composition of claim 1, further comprising at least one solvent.

15. The vaporizable alkaloid composition of claim 14, wherein the at least one solvent is selected from the group consisting of propylene glycol, water, ethanol, glycerin, and mixtures thereof.

16. The vaporizable composition of claim 14, wherein the solvent is selected from the group consisting of propylene glycol, glycerin, ethanol, and mixtures thereof.

17. The vaporizable alkaloid composition of claim 1, wherein the molar ratio of total substituted pyridine compound to total organic acid is about 50:1.

18. The vaporizable alkaloid composition of claim 1, further comprising at least one chemosensory irritant and at least one solvent.

19. The vaporizable alkaloid composition of claim 1, further comprising at least one chemosensory irritant and at least on flavoring agent.

20. The vaporizable alkaloid composition of claim 1, further comprising at least one solvent and at least one flavoring agent.

21. The vaporizable alkaloid composition of claim 1, further comprising at least one chemosensory irritant, at least one solvent, and at least one flavoring agent.

22. The vaporizable alkaloid composition of claim 1, in an alkaloid dispensing pouch, e-cigarette or electronic nicotine delivery system.

23. The vaporizable alkaloid composition of claim 22, wherein the alkaloid dispensing pouch is adapted for release of the alkaloid therefrom.

24. The vaporizable alkaloid composition of claim 1, further comprising from about 0.0001 wt. % to about 0.50 wt. % of a spice additive having a spiciness of from about 1,000 to about 20,000,000 Scoville Heat Units (SHU).

25. The vaporizable composition of claim 1, wherein the at least one organic acid consists of a mixture of citric acid and acetic acid.

26. A vaporizable alkaloid composition, comprising:
at least one substituted pyridine compound of Formula (I), or salt or mixed salt thereof;

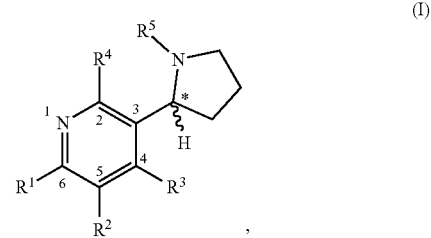

wherein $R^5$ is $CH_3$, and $R^1$, $R^2$, $R^3$, and $R^4$ are independently selected from alkyl, H, substituted alkyl, cycloalkyl, substituted cycloalkyl, alkenyl, and substituted alkenyl, with the proviso that at least one of $R^1$, $R^2$, $R^3$, and $R^4$ is not H,
at least one organic acid,
wherein the vaporizable alkaloid composition is entirely devoid of (R) or(S) nicotine wherein the organic acid is selected from the group consisting of formic acid, acetic acid, trifluoroacetic acid, aspartic acid, butanoic acid, butyric acid, 2-methylbutyric acid, 3-methylbutyric acid, benzoic acid, caprylic acid, crotonic acid, ethylenediaminetetraacetic acid, fumaric acid, gluconic acid, glutamic acid, glyceric acid, glycolic acid, lactic acid, lauric acid, levulinic acid, maleic acid, malonic acid, mandelic acid, methane sulfonic acid, oxalic acid, phenylacetic acid, phthalic acid, picric acid, propionic acid, pyruvic acid, salicylic acid, stearic acid, tannic acid, tartronic acid, valeric acid, and mixtures thereof.

27. The vaporizable alkaloid composition of claim 26, wherein the organic acid is selected from the group consisting of citric acid, acetic acid, benzoic acid, tartaric acid, lactic acid, salicylic acid, malic acid, levulinic acid, and mixtures thereof.

28. The vaporizable composition of claim 26, further comprising citric acid, malic acid, succinic acid, tartaric acid, and mixtures thereof.

29. A vaporizable alkaloid composition comprising:
from about 1 wt. % to about 80 wt. % of(S)-2-methyl-5-(1-methylpyrrolidin-2-yl) pyridine;—
from about 0.05 wt. % to about 1.5 wt. % in total of at least one organic acid;
and
remainder solvent,
wherein the weight percentages are based on the total weight of the vaporizable alkaloid composition; and
wherein the molar ratio of moles of(S)-2-methyl-5-(1-methylpyrrolidin-2-yl) pyridine to total moles of organic acid is from about 25:1 to about 75:1.

* * * * *